United States Patent [19]
Garcia et al.

[11] Patent Number: 5,876,463
[45] Date of Patent: Mar. 2, 1999

[54] COMPOSITIONS FOR COLORING KERATINOUS FIBERS COMPRISING SULFO-CONTAINING, WATER DISPERSIBLE COLORED POLYMERS

[75] Inventors: Mario L. Garcia, Stamford, Conn.; James J. Krutak, Kingsport, Tenn.; Keith C. Brown, New Canaan, Conn.; Dante J. Rutstrom, Kingsport, Tenn.

[73] Assignee: Bristol-Myers Squibb Company, New York, N.Y.

[21] Appl. No.: 761,410

[22] Filed: Dec. 6, 1996

Related U.S. Application Data

[63] Continuation-in-part of Ser. No. 476,303, Jun. 7, 1995, Pat. No. 5,735,907.

[51] Int. Cl.$^6$ ...................................................... A61K 7/13
[52] U.S. Cl. .......................... 8/405; 8/552; 8/557; 8/562; 8/564; 8/647
[58] Field of Search ................................ 8/404, 405, 552, 8/557, 562, 564, 647; 525/420, 421, 434, 435, 437, 436; 528/290, 293, 294, 295

[56] References Cited

U.S. PATENT DOCUMENTS

| | | | |
|---|---|---|---|
| 3,619,101 | 11/1971 | Kalopissis | 8/426 |
| 4,314,808 | 2/1982 | Jacquet et al. | 8/405 |
| 4,339,237 | 7/1982 | Wang et al. | 8/405 |
| 4,471,079 | 9/1984 | Enami | 523/161 |
| 4,763,371 | 8/1988 | Parton | 8/647 |
| 4,804,719 | 2/1989 | Weaver et al. | 525/420 |
| 4,911,731 | 3/1990 | Loveless | 8/405 |

*Primary Examiner*—Paul Lieberman
*Assistant Examiner*—Caroline D. Liott
*Attorney, Agent, or Firm*—Anthony M. Santini; Charles J. Zeller

[57] ABSTRACT

Compositions for coloring keratinous fibers comprising a sulfo-containing, water-dispersible polymer having carbonyloxy linking groups, and a colorant reacted into or onto the polymer backbone.

18 Claims, No Drawings

COMPOSITIONS FOR COLORING KERATINOUS FIBERS COMPRISING SULFO-CONTAINING, WATER DISPERSIBLE COLORED POLYMERS

This application is a Continuation-In-Part of U.S. Ser. No. 08/476,303, filed Jun. 7, 1995, now U.S. Pat. No. 5,735,907.

BACKGROUND OF THE INVENTION

1. Field of the Invention

This invention relates to compositions and processes for non-permanently coloring keratinous fibers, particularly human hair, comprising the use of sulfo-containing, water-dispersible, colored polymers wherein the colorant moiety is incorporated into or onto a carbonyloxy and/or carbonylamide backbone of the polymer. The compositions preferably additionally comprise nonionic hydrophobically modified associative thickeners. The colored polymers are uniquely designed to offer cosmetically desirable color coatings on hair and to be easily dispersible in hot water, yet offer excellent resistance to redispersion in water at room temperature, which prevents color bleeding if the hair becomes wet while colored with the polymers. It may be further desirable to thicken these dispersions in order to prevent dripping or running of the dispersion during application. In addition, in some applications, thick lotions and gels can be advantageously used to apply colored polymer dispersions to hair. We have found that nonionic, hydrophobically modified associative thickeners can be conveniently used to increase product viscosity without significantly compromising the performance of the colored polymers.

2. Description of the Prior Art

It is very desirable to offer users of hair colorants the option of coloring their hair in such a manner that the effect of the coloring treatment can be easily removed or reversed by the use of regular, commercial shampoo products. Uncertainty and concern about selecting the right color, the wish to easily experiment with different hair tonalities, and the changing requirements of fashion and lifestyles, all contribute to the desirability of non-permanent hair coloring products. Additionally, there is a frequent need to modulate or adjust the color produced by prior, more permanent color treatments. This is especially desirable in order to compensate for the gradual color fading which is always observed after using even the most permanent hair coloring products.

Another application for hair coloring materials which can easily and reversibly color hair comprises incorporating them into frequently used hair care products such as conditioners, mousses and setting lotions. This allows the user to conveniently tone or introduce color highlights in the hair without the need for a separate coloring process.

Customarily, hair is colored using low molecular weight compounds which penetrate the keratinous fibers. This approach has been successful for producing permanent and semipermanent color effects on hair. It requires, however, some affinity between the chromophore-bearing molecules of the colorant and the fibers and, as a result, it becomes very difficult even after repeated shampooing to remove all the colorant which has penetrated into the hair. In addition, these permanent and semi-permanent treatments are very sensitive to variations in the quality of hair among different individuals. Treatments which do not penetrate the hair fibers, but which color hair by depositing colored materials only on the hair fiber surface, are practically insensitive to such variations, can be easily removed and have therefore been proposed and used for the non-permanent, i.e. totally reversible, coloring of hair.

U.S. Pat. No. 4,559,057 describes the use of insoluble pigments. Due to their poor adherence to the hair surface, they are to be used together with a polymeric binder in order to reduce rub-off of the color and produce acceptable color coatings on hair. Insoluble pigments are very different from the soluble dyes of the present invention.

U.S. Pat. No. 4,804,719 discloses polymeric compositions which contain carbonyloxy and carbonylamide links, particularly polyesters and polyesteramides, having water solubilizing sulfonate groups and colorants, copolymerized onto or into the polymer backbone. It is indicated in this patent that these polymers are useful in adhesives, coating materials, films and packaging materials. It is also stated therein that aqueous dispersions of these materials have utility as inks, paints and other industrial coatings, all of which are intended to be permanent in nature. No disclosure is made relating to the specific art of dyeing keratinous fibers, non-permanently or otherwise.

Various examples of thermally stable industrial colorants useful for manufacturing colored polymers through incorporation into or onto the sulfopolyester polymer are described in U.S. Pat. Nos. 2,571,319; 3,034,920; 3,104,233; 3,372,138; 3,417,048; 3,489,713; 3,278,486; 3,359,230; 3,401,192; 3,417,048; 3,424,708; 4,049,376; 4,080,355; 4,088,650; 4,116,923; 4,141,881; 4,202,814; 4,231,918; 4,267,306; 4,279,802; 4,292,232; 4,344,767; 4,359,570; 4,403,092; 4,477,635; 4,594,400; 4,617,373; 4,617,374; 4,740,581; 4,745,173; 4,808,677; 4,892,922; 4,892,923; 4,958,043; 4,999,418; 5,030,708; 5,032,670; 5,075,491; 5,086,161; 5,102,980; 5,106,942; 5,151,516; 5,179,207; 5,194,571; 5,274,072; 5,281,658 and 5,384,377. None of the above references suggest the application of the industrial colorants to human hair.

U.S. Pat. Nos. 4,300,580 and 5,158,762 disclose hair spray compositions comprising colorless, sulfo-containing, water dispersible polyesters which are useful for giving hair a firm texture and for holding hair in a desired arrangement for a certain length of time. These polymers are fundamentally different from those in the present invention in that the reference does not teach or suggest colored molecules. Inherently, they also fail to suggest incorporating colored molecules into or onto the polymeric backbone.

In order for colored polymers to be useful in non-permanent hair coloring they must fulfill a number of requirements which are quite distinct from those necessary for hair spray resins. Specifically, they must form films that strongly adhere to the hair surface. Such films must also remain flexible enough under different temperature and relative humidity conditions so as to withstand the bending of hair without fracturing and separating from the fibers. They should, however, be hard enough to prevent the transfer of color if rubbed against parts of the body, clothing, etc. They must be easily and completely removable by shampooing and yet, in order to prevent color bleed, they cannot be easily redispersed or resolubilized by contact with water at room temperature. They must also obviously be safe and not irritate or stain the skin. In contrast, hair spray and other hair styling colorless polymers are practically invisible to the naked eye. As a result, rub-off onto other surfaces, moderate flaking of fractured film particles, incomplete shampoo removability, and "bleed" upon exposure to water would not be noticed.

Unlike the aforementioned colorless polymers, the intense coloration of the polymers described in this invention would make even small-trace quantities of them quite obvious, and easily noticeable on hair, other surfaces and in solution. It can thus be easily understood that the requirements for hair spray or hair styling colorless polymers are intrinsically far less stringent than those for colored polymers for use in non-permanent hair coloring products. It is then by no means anticipated that, if a certain type of colorless polymer useful in hair fixatives could be made colored even without changing its properties, it would then also be advantageously useful for non-permanent hair coloring. It is moreover well known to those familiar with polymer chemistry and properties that it is extremely difficult to incorporate a new and different comonomer into or onto a polymer backbone without substantially changing the properties of the polymer.

U.S. Pat. No. 3,251,743 to BASF and U.S. Pat. Nos. 3,535,255; 3,567,678; 3,597,468; 3,617,165; 3,619,101; 3,720,653; 3,763,086; 3,797,994 and 3,915,635 to L'Oreal disclose colored polymers and compositions for coloring hair. These polymers are structurally different from those disclosed in the present invention in that they do not have solubilizing sulfonate groups and they have a hydrocarbon backbone. They rely instead on carboxy groups which in some cases have to be neutralized by organic or inorganic bases in order to make these polymers water soluble. Alternatively, they can be dissolved in alcohol or alcohol-water solutions.

U.S. Pat. No. 4,182,612 describes a new class of water soluble cationic colored polymers useful for dyeing hair prepared by the colorant reaction of chromophores with selected polymer backbones. U.S. Pat. No. 4,228,259 also describes the preparation and use for dyeing hair of water soluble cationic colored polymer having various amine groups wherein said amine groups are either a part of or aid in the linking to the polymer chain of an aryl or arylaliphatic chromophore. The polymers in both of these patents are different from those in the present invention in that they do not have water solubilizing sulfonate groups and the structure of the backbone is very different. In addition, and by design, their cationic nature gives them a very strong affinity for hair, making them very shampoo resistant and therefore not suitable for temporary, i.e. easily removable, hair coloring treatments.

U.S. Pat. Nos. 4,051,138; 4,144,252; and 4,169,203 to Dynapol describe the composition of water soluble colored anionic polymers. These polymers are different from those of the present invention in various important respects. The polymer backbone is a simple hydrocarbon chain whereas the polymers described in this invention contain carbonyloxy and/or carbonylamide moieties in the backbone. Although the polymers in these three patents similarly have water solubilizing sulfonate groups, these polymers were mainly designed to be used as water soluble colorants in foods and beverages and are so readily and quickly water soluble that they would show excessive color bleeding if used to color hair. In addition, they are not good film forming polymers and, because of these characteristics, they are not useful as substantive hair colorants. In contrast, since the sulfo-containing polymers of the present invention are not readily water-soluble, less bleeding is observed. Thus, they are a major improvement over the Dynapol compounds.

In summary, the colored polymers used in this invention have chemical structures different from the colored polymers proposed as hair colorants in the prior art. The combination of the water-solubilizing sulfonate groups, colored monomers, and the structure of the polymer backbone, which may include three to four additional monomers, is unique. Unexpectedly, this type of structure produces colored polymers which are highly resistant to dispersion in ambient temperature water. As a result, when these polymers are present on the hair surface as dry films, color bleed upon exposure to ambient temperature water is insignificant.

It is well known that the viscosity of hair cosmetic products is usually adjusted in order to facilitate performance and ease of application. When such products are designed for use on the scalp, their viscosity must be sufficiently low so that they can be easily and uniformly distributed throughout the relatively large mass of hair, but not so low that the product will drip or flow on the face, neck, etc. of the user. In other cases, as when treating various types of facial hair, higher viscosity may be desirable. These considerations are especially important for hair coloring products, as usually they must remain on the hair for a relatively long time in order for dyeing to take place. A wide variety of both natural and synthetic viscosity increasing agents (thickeners) are commercially available for use in hair products and in haircoloring products in particular.

U.S. Pat. No. 3,811,830 discloses compositions for the semipermanent dyeing of hair and mentions a series of thickeners which are suitable for this application. These include hydroxybutylcellulose, hydroxyethylcellulose, methyl cellulose, sodium carboxymethylcellulose, sodium alginate, and magnesium aluminum silicate. Semipermanent haircoloring compositions produce coloring effects which only survive a relatively small number of shampooings, and do not require the use of an oxidizing agent to develop the color. With permanent oxidative hair coloring compositions, the coloration imparted to the hair is relatively insensitive to repeated shampooing. Oxidative hair coloring products comprising intermediates and couplers usually involve the use of a two part system. The rheology of many such products is usually adjusted by the use of a low viscosity dye lotion which in addition to the intermediates and couplers contains a high level of surfactants and organic solvents, and which upon mixture with a highly aqueous solution of the oxidizing agent forms a dye mixture with the desired gel-like consistency. U.S. Pat. Nos. 3,388,627; 4,563,188; 5,503,640; 5,518,505; 5,500,021 disclosing oxidative hair dyeing compositions exemplify this approach. These patents also mention various thickeners including sodium alginate, gum arabic, cellulose derivatives, such as methylcellulose hydroxyethylcellulose, sodium carboxymethylcellulose, acrylic polymers, such as the sodium salt of polyacrylic acid, and inorganic thickeners, such as bentonite, which can be used to further adjust the viscosity of this type of product.

A third category of hair coloring products is based on temporary coloring of human hair. The coloring effects produced by these products can be easily removed by shampooing the hair once. Whereas both semipermanent and permanent hair coloring products are normally rinsed off the hair after the treatment is completed, temporary hair coloring products may be advantageously allowed to remain on the hair after application. When products are rinsed following application, thickeners do not have to perform beyond this stage. On the other hand, with no-rinse non-permanent hair coloring products, as is the case in the present invention, the thickener and all the other product ingredients are left on the hair surface after product application. In this instance, any of these ingredients may have an effect on the feel, appearance and behavior of the treated hair, as well as on the physical properties of colored deposit which is left on the fiber surface. As a result, the selection of product adducts for a leave-on product, can present unique technical difficulties. In the case of thickeners, the materials must not only perform well during application, but must also not negatively interfere with the overall aftertreatment performance of the product.

U.S. Pat. Nos. 3,251,743; 3,535,255; 3,567,678; 3,597,468; 3,617,165; 3,619,101; 3,720,653; 3,763,086; 3,797,994; 3,915,635; and 4,182,612 referred to above, which disclose colored polymer compositions and methods for the temporary coloring of hair, mention that the compositions may contain additional colorless polymers to adjust the physical properties of the dyeing systems, and/or other additives conventionally used in such cosmetics, but do not make reference to any specific type of thickener which could advantageously be used in the practice of those inventions.

U.S. Pat. No. 4,228,259 which discloses "Water Soluble Cationic Polymer Dye Compounds and Process for Producing Same", mentions thickening agents which can be cellulosic derivatives such as carboxymethylcellulose, hydroxypropylmethylcellulose and hydroxyethylcellulose.

Thickeners which differ from the ones referred to in the above patents are the hydrophobically modified associative thickeners. By "hydrophobically modified associative thickeners" is meant ionic or nonionic colorless, hydrophilic, water soluble polymers which have been modified by the incorporation of a sufficient amount of hydrophobic substituents either into their backbone or as side groups in order to make the polymers less water soluble allowing them to function as viscosity increasing agents. The degree of hydrophobic substitution is kept small in order not to render the modified polymer water insoluble. Aqueous solutions of these polymers have unusual rheological properties which are thought to arise from intermolecular associations of neighboring hydrophobic groups. These associations give rise to the formation of reversible three dimensional network structures. The regions of intermolecular hydrophobic association are also areas of high affinity for surfactant interactions. At low concentrations, surfactants interact mainly with the hydrophobic segments of the polymer, strengthening the network and producing an increase in the viscosity of the system. At higher concentrations, the hydrophobic segments of the polymer are solubilized within surfactant micelles, the network is destabilized and viscosity decreases. [See: "Surfactant Interactions with HUER Associating Polymers" and references therein, Kewei Zhang, Bai Xu, Mitchell A. Winnik and Peter M. MacDonald, The Journal of Physical Chemistry, 1996, 100, pages 9834–9841].

U.S. Pat. No. 4,155,892, ("Polyurethane Thickeners for Aqueous Compositions") assigned to Rohm and Haas Company, discloses aqueous systems which are thickened by incorporation of nonionic polyurethanes having at least three low molecular weight hydrophobic groups. The hydrophobic groups together contain a total of at least 20 carbon atoms and are linked through hydrophilic (water soluble) groups containing polyether segments of at least about 1500 molecular weight. The molecular weight of these polyurethanes is of the order of about 10,000 to 200,000.

Claimed in this patent are compositions comprising these polymers and "a cosmetically active material". Rohm and Haas trade literature on Aculyn® 44, an example of this type of compound, recommends the use of these materials in various cosmetic compositions including hair conditioners, aqueous antiperspirants, silicone emulsions, oxidizer containing hair dyes and cationic and sunscreen lotions.

U.S. Pat. No. 5,478,562, ("Cosmetic Composition Containing at Least One Surface-Active Agent of the Alkly Polyglycoside and/or Polyglycerolated Type and at Least One Polyurethane") assigned to L'Oreal, discloses cosmetic compositions containing the aforementioned surface agents and hydrophobically modified associative polyurethanes thickeners of the type disclosed in the Rohm and Haas patent. Compositions and processes for the washing and treatment of hair and skin are among the claims of the L'Oreal patent. The compositions of the present invention do not include surface active agents of the alkyl polyglycoside or polyglycerolated type.

A second type of hydrophobically modified associative thickener consists of certain nonionic modified cellulosic ethers. These materials which are disclosed in U.S. Pat. No. 4,228,277 assigned to Hercules Incorporated, have relatively low molecular weights but are capable of producing highly viscous aqueous solutions in practical concentrations. These materials have a sufficient degree of nonionic substitution selected from the groups consisting of methyl, hydroxyethyl and hydroxypropyl to cause them to be water soluble and are further substituted with a hydrocarbon radical having from about 10 to 24 atoms in amounts between about 0.2 weight percent and the amount which renders the cellulose ether less than 1% by weight soluble in water.

This patent teaches the use of these materials in shampoo formulations. Technical literature from the AQUALON Company teaches the use of these materials in hand and body lotions, shampoos and liquid soaps. U.S. Pat. No. 4,683,004, ("Foamable Compositions and Processes for Use Thereof") assigned to Union Carbide Corporation, discloses the use of the above materials in compositions for cosmetic applications to hair and skin which, in addition to the AQUALON thickeners, comprise one or more of a surfactant, a water-miscible alcohol, an oil emulsified in the water of the foamable composition, and a water soluble moisturizer. The compositions of the present invention do not comprise an emulsified oil or a water soluble moisturizer.

U.S. Pat. No. 5,100,657 (The Procter & Gamble Co.) claims hair conditioning compositions, the most relevant of which comprise: (a) hydrophobically modified cellulosic associative thickeners of the type disclosed in U.S. Pat. Nos. 4,228,277 (HMCAT-'277), a water insoluble surfactant, a compatible solvent, a silicone conditioning agent, and a fatty aclohol, and (b) (HMCAT-'277), hydrogenated tallow amide DEA, a chelating agent, water, a combination of a volatile silicone fluid and a silicone gum, dihydrogenated tallow dimethyl ammonium chloride, and a fatty alcohol. It also claims methods for providing conditioning to hair comprising treating the hair with the above compositions. The compositions of the present invention do not comprise most of the ingredients included in the compositions claimed in this patent.

U.S. Pat. No. 5,100,658 (The Procter & Gamble Co.) claims hair cosmetic compositions, the most relevant of which comprise: (a) a hydrophobically modified nonionic water soluble polymer which comprises a water soluble backbone and hydrophobic groups selected from the group consisting of $C_8$–$C_{12}$ alkyl, aryl alkyl and alkyl aryl groups and mixtures thereof, wherein the ratio of the hydrophilic portion to the hydrophobic portion of the polymer is from about 10:1 to about 1000:1, a water soluble polymeric thickener, a compatible solvent, and an active cosmetic component selected from the group consisting of conditioning agents, antidandruff aids, hair growth promoting aids, perfumes, dyes, pigments, sunscreens, hair holding polymers, and mixtures thereof; and (b) same as (a), but where the hydrophobically modified polymer is a HMCAT-'277. The compositions of the present invention do not comprise most of the ingredients included in the compositions claimed in this patent.

U.S. Pat. No. 5,104,646 (The Procter & Gamble Co.) claims hair cosmetic compositions, the most relevant of which comprise: (a) a hydrophobically modified nonionic water soluble polymer which comprises a water soluble backbone and hydrophobic groups selected from the group consisting of $C_8$–$C_2$ alkyl, aryl alkyl and alkyl aryl groups and mixtures thereof, wherein the ratio of the hydrophilic portion to the hydrophobic portion of the polymer is from about 10:1 to about 1000:1, a water insoluble surfactant, a compatible solvent, and an active cosmetic component selected from the group consisting of conditioning agents, antidandruff aids, hair growth promoting aids, perfumes, dyes, pigments, sunscreens, hair holding polymers, and mixtures thereof; (b) same as (a), but where the hydrophobically modified polymer is a HMCAT-'277; (c) a HMCAT-'277, a water insoluble surfactant, a chelating agent, a distributing aid selected from the group consisting of xanthan gum and dextran, a compatible solvent, and an active hair care component; (d) a HMCAT-'277, a water insoluble surfactant, a compatible solvent, and an active hair care component comprising a silicone conditioning agent and fatty alcohol; and (e) a HMCAT-'277, hydrogenated tallow amide DEA, a chelating agent, an active hair care component, a silicone conditioning agent, dehydrogenated tallow dimethyl ammonium chloride and a fatty alcohol. The compositions of the present invention do not comprise most of the ingredients included in the compositions claimed in this patent.

U.S. Pat. No. 5,106,609 (The Procter & Gamble Co.) claims hair cosmetic compositions, the most relevant of which comprise: (a) a hydrophobically modified nonionic water soluble polymer which comprises a water soluble backbone and hydrophobic groups selected from the group consisting of $C_8$–$C_{12}$ alkyl, aryl alkyl and alkyl aryl groups and mixtures thereof, wherein the ratio of the hydrophilic portion to the hydrophobic portion of the polymer is from about 10:1 to about 1000:1, a water insoluble surfactant, a compatible solvent, and an active cosmetic component; (b) same as (a), but where the hydrophobically modified polymer is a HMCAT-'277; (c), same as (b), but additionally comprising a water soluble polymer material having a molecular weight greater than about 20,000; (d) same as (b), but additionally comprising a chelating agent; (e) same as (c), but additionally comprising a chelating agent; (f) same as (b), were the said active cosmetic component comprises an active hair care component; (g) same as (e), wherein the active hair care component is selected from the group consisting of conditioning agents, antidandruff aids, hair growth promoters, perfumes, dyes, pigments, hair holding polymers, and mixtures thereof; (h) same as (f), wherein the haircare components are various types of silicone materials; and (i) other compositions comprising related combinations. The compositions of the present invention do not comprise most of the ingredients included in the compositions claimed in this patent.

A third type of hydrophobically modified associative thickener are the hydrophobically modified polyacrylates. A commercially available example is Aculyn 22® which is described in the Rohm and Haas Company trade literature as a hydrophobically modified associative acrylic polymeric thickener containing acid carboxyl (anionic) functional groups. The same literature recommends the use of Aculyn 22® in hair styling gels, foaming facial cleansers, specialty shampoos, curl activators, and depilatories. Carbopol® ETD 2020 from B. F. Goodrich is another example of a commercially available anionic hydrophobically modified polyacrylic acid thickener. U.S. Pat. No. 5,376,146 discloses a system for adjusting the viscosity of an oxidative dye system which relies on a pH change on mixing an alkaline dye lotion, with a low pH oxidative agent solution which includes Aculyn 22® which is insoluble in the oxidative agent solution, but dissolves to form a gel when mixed with alkaline dye lotion.

Hydrophobically modified cationic thickeners like Quatrisoft Polymer LM 200, an alkyl modified hydroxyethyl cellulose quaternary from Union Carbide Chemicals and Plastics Co. Inc., are commercially available. Due to their cationic nature these materials are not compatible with the anionic colored polymers described in this invention.

We have found that whereas many polymeric thickeners significantly reduce the resistance to redispersion in room temperature water of the colored polymers described in this invention, surprisingly, nonionic hydrophobically modified associative thickeners either by themselves or in combination with some surfactants can be conveniently used to increase product viscosity without compromising the bleed resistance and other important performance properties of such polymers when used in the temporary coloring of hair. We find that whereas the use of hydrophobically modified thickeners has been amply described in the patent literature, we find no prior art which anticipates the unique and unexpected properties of compositions comprising the colored polymer described in this invention, particularly in combination with nonionic hydrophobically modified associative thickeners.

SUMMARY OF THE INVENTION

It is the purpose of this invention to provide a fast and convenient method and a hair coloring composition for non-permanently coloring hair. The hair coloring composition comprises a colored, sulfo-containing, water-dispersible polymer having carbonyloxy and/or carbonylamide links and has the colorant moiety incorporated into or onto the backbone of the polymer by covalent bonds. Other water-dispersible or water-soluble polymers, in particular nonionic hydrophobically modified associative thickeners, may be present. The colored polymer may be formulated into conventional type hair care systems such as mousses, gels, sprays and lotions.

It is further a purpose of this invention to provide a fast and convenient composition and method for non-permanently coloring hair with a full range of color shades and which can be easily and completely removed by simple shampooing.

It is another object of the invention to provide compositions and a method for non-permanently coloring hair, wherein the colored hair shows minimal color bleed upon exposure to ambient temperature water, virtually no color rub-off and excellent resistance to flaking during combing and brushing.

It is also a purpose of the present invention to provide compositions and a method for non-permanently coloring hair involving the use of colored polymers which are readily dispersed in hot (e.g., above about 80° C.) water without the assistance of detergents, organic cosolvents, or organic or inorganic bases, thus eliminating their exposure to the user and their contaminating effect on the environment.

It is yet another purpose of this invention to provide compositions and a fast method for non-permanently coloring hair which does not stain the skin, which is safe, and which minimizes the exposure to the user of low molecular weight colored compounds.

It is another purpose of this invention to provide compositions for non-permanent hair coloring which can be easily removed by simple shampooing, but if so desired can be made more permanent to last through several (i.e., 6–8) shampooings by a subsequent rinse of the colored hair with an aqueous solution of inorganic salts, such as bi-valent and tri-valent ions (e.g., $Fe^{+++}$, $Al^{+++}$, $Mg^{++}$, $Ca^{++}$).

It is an additional object of the invention to provide a composition which can be conveniently used as a color refresher to compensate for the gradual color fading observed after more permanent color treatments.

It is another object of the present invention to provide compositions which can be readily used to non-permanently color hair in a way which makes it appear lighter in color.

Lastly, it is yet one more object of this invention to provide multiple purpose compositions and methods to non-permanently color hair and at the same time provide other benefits such as hair setting, styling and hair conditioning in one single treatment.

DETAILED DESCRIPTION OF THE INVENTION

It has been surprisingly discovered that colored polymers similar to those described in the Background of the Invention relating to industrial applications can be advantageously used for the temporary surface coloring of keratinous fibers, particularly human hair. This result is unexpected due to the important differences in chemical composition and properties between the surface of keratin fibers and the surfaces of cellulose based papers, containers and other man-made substrates onto which inks and paints are normally applied. Adequate wetting adhesion and film formation on the latter surfaces are no predictors of performance on the surface of human hair. In addition, other properties such as ease of removal from the hair by shampooing, resistance to brushing and absence of scalp staining could not have been anticipated from their industrial use as inks, paints or coatings, particularly since such applications are intended to be and are permanent.

The resistance of the polymers described in this invention to bleed when in contact with room temperature water has been carefully balanced with their ease of removability by shampooing.

As mentioned above, this makes them especially suitable for non-permanent colorings. This finely tuned behavior makes the properties of their dry films very sensitive to the presence of other compounds, especially if these compounds strongly interact with water. Most water soluble polymeric thickeners owe their ability to extensive association with water molecules. It is thus not surprising that most of the water soluble polymeric thickeners commonly used in hair products would, when jointly used, reduce the intrinsic bleed resistance of the colored polymers described in this invention. Nonionic hydrophobically modified associative thickeners are also water soluble, however, and the good bleed resistance when used in combination with the colored polymers described in this invention was thus surprising and unexpected. Also unexpected is the minor effect on bleed resistance of some of the surfactants which can be added to compositions in order to produce additional increases in viscosity.

It should be emphasized that resistance to color bleeding is just one of the critical parameters associated with the good performance of a leave-on haircoloring product. Other equally important attributes are shampoo removability, insignificant rub-off, good feel, appearance and behavior of the colored hair. The nonionic hydrophobically modified associative thickeners comprised in the compositions disclosed in this invention do not significantly compromise the excellent properties, in terms of the above attributes, exhibited by the colored polymers of the present invention when used by themselves.

It should also be noted that, in practice, the flow properties, ease of application and feel of the product is not completely determined by its viscosity. The range of compositions disclosed in this application are meant as guidelines which offer ample flexibility to formulating haircoloring products with the colored polymers disclosed in this invention.

The non-permanent coloration of hair is conveniently, quickly and safely provided by the composition of the present invention which, in its broadest sense, comprises a tinctorially effective amount of a colored, sulfo-containing, water-dispersible polymeric material having carbonyloxy linking groups, wherein the colorant moiety is reacted into or onto the polymeric backbone. The linking groups may further comprise carbonylamide linking groups, provided at least about 20 mole % of the linking groups are carbonyloxy linking groups. Preferably, the polymer contains water-solubilizing sulfonate groups and the colorant comprises one or more heat stable organic compounds initially having at least one condensable group, wherein the colorant is present in an amount from about 1 to about 40 mole %, based on the total of all reactant hydroxy, carboxy and amino equivalents. These equivalents encompass the various condensable derivatives thereof including carbalkoxy, carbaryloxy, N-alkycarbamyloxy, acyloxy, chlorocarbonyl, carbamyloxy, N-(alkyl)$_2$carbamyloxy, alkylamino, N-phenylcarbamyloxy, cyclohexanoyloxy and carbocyclohexyloxy. The term "heat stable" is intended to mean stable up to at least about 270° C.

In a more preferred embodiment, the polymer useful in the present invention contains about 20 to about 100 mole % carbonyloxy linking groups in a linear molecular structure and 0 to about 80 mole % carbonylamide linking groups, the polymer having a weight average molecular weight of from about 5,000 to about 50,000, more preferably from about 10,000 to about 25,000, and an inherent viscosity of from about 0.10 to about 0.50 measured in a 60/40 parts by weight solution of phenol/tetrachloroethane at 25° C. and at a concentration of 0.10 g. of polymer in 100 ml of the solvent, the polymer containing substantially equimolar proportions of acid equivalents (100 mole percent) to hydroxy and amino equivalents (100 mole percent), the polymer comprising the reaction residues of the following reactants (a), (b), (c), (d) and (e), and the ester-forming and esteramide-forming derivatives thereof:

(a) at least one dicarboxylic acid;

(b) from about 4 to about 25 mole %, based on a total of all acid, hydroxy and amino equivalents being equal to about 200 mole %, of at least one difunctional sulfomonomer containing at least one sulfonate group attached to an aromatic or cycloaliphatic nucleus wherein the functional groups are hydroxy, carboxy or amino;

(c) at least one difunctional reactant selected from a glycol or a mixture of a glycol and diamine having two —NHR groups, the glycol containing two —CH$_2$OH groups of which (1) at least about 10 mole %, based on the total mole percent of hydroxy or hydroxy and amine equivalents, is a poly(ethylene glycol) having the structural formula:

n being an integer of from about 2 to about 20, or
(2) from about 0.1 to about 15 mole %, based on the total mole percent of hydroxy or hydroxy and amine equivalents, is a poly(ethylene glycol) having the structural formula:

$H(OCH_2CH_2)_nOH$ n being an integer of from about 2 to about 500, and with the proviso that the mole percent of said poly (ethylene glycol) within said range is inversely proportional to the quantity of n within said range;

(d) optionally, at least one difunctional reactant selected from a hydroxycarboxylic acid, an amino-carboxylic acid having one —NHR group and an amino-alcohol having one —C(R)$_2$OH group and one —NHR group; or mixtures of said difunctional reactants; wherein each R in the (c) or (d) reactants is a hydrogen atom or alkyl group of 1 to 4 carbon atoms; and (e) from about 5 mole % to about 40 mole %, based on a total of all acid, hydroxy and amino equivalents being equal to about 200 mole %, of one or more thermally stable colorant(s) having at least one functional group selected from hydroxy, carboxy and amino equivalents, and the condensable derivatives thereof, reacted into or onto the polymer chain.

In a further preferred embodiment, the carbonyloxy linking groups are polyesters and the carbonylamide linking groups, if any, are polyesteramides.

In a most preferred embodiment, the sulfo-containing polyester contains not more than about 10 mole %, based on all reactants, of reactant (d); about 5 to about 30 mole %, based on all reactants, of reactant (e); and at least 70 mole % of all hydroxy equivalents are present in the glycol.

The use of the term "acid" in the above description of the polymer includes the various ester forming or condensable derivatives of the acid reactants such as the acid halides and methyl esters as employed in the preparations set out in the patents incorporated herein by reference. Among the preferred sulfomonomers are those wherein the sulfonate group is attached to an aromatic nucleus such as benzene, naphthalene, diphenyl and/or the like.

Suitable thermally stable colorants are described in the aforementioned prior art references, such as U.S. Pat. No. 4,804,719, the disclosure of which is incorporated herein by reference, and preferably selected from the classes of:

methines; bis-methines; anthraquinones; 3H-dibenz[f,ij] isoquinoline-2,7-diones(anthrapyridones); triphenodioxazines; 5,12-dihydroquinoxalino[2,3-b]phenazines (fluorindines); phthaloylpyrrocolines; 2H-1-benzopyran-2-ones(coumarins); 3H-naphtho[2,1-b] pyran-2-ones(benzocoumarins); 4-amino-1,8 naphthalimides; thioxanthene-9-ones; 2,5(3)-arylaminoterephthalic acids (or esters); benzo[f]pyrido [1,2-a]indole-6,11-diones; quinophthalones; 7H-benz (de)anthracene-7-ones(benzanthrones); 7H-benzo[e] perimidin-7-ones(anthrapyrimidines); 6,15-dihydro-5, 9,14,18-anthrazinetetrones(indanthrones); 7H-dibenz [f,ij]isoquinoline-7-ones(anthrapyridines); 6H,18H-pyrido[1,2-a:3,4-b']diindole-6,13-diones, diindolo[3,2, 1-de:3',2',1'-ij][1,5]naphthpyridin-6,13-diones; naphtho[1',2',3':4,5]quino[2,1-b]quinazoline-5,10 diones; benzo[f]pyrido[1,2-a]indole-6,11-diones; 7H-benzimidazo[2,1-a][de]isoquinolin-7-one; 5H-benzo[a]phenoxazine-5-ones; 5H-benzo[a] phenothiazine-5-ones; benzo[f]pyrido[1,2-a]indole-6, 11-diones; 3,6-diaminopyromellitic acid diimides; naphthalene[1:4:5:8]tetra carboxylic bis imides; 3-aryl-2,5-dioxypyrrolines; perinones; perylenes; phthalocyanines; anthraisothiazoles; quinacridones; anthrapyrimidones; phthaloylacridones; phthaloylphenothiazines and phthaloylphenothiazine-S,S-dioxides.

Particularly preferred classes of colorants are the methines, bis-methines, anthrapyridones, anthraquinones and phthalocyanines.

The colorant compounds described above may be represented by the formula:

X—Col—X wherein Col is the residue of one of the types of colorants set forth above and X is a condensable carbonyloxy—reactive or carbonylamide-reactive substituent, i.e., a group reactive with at least one of the monomers from which the sulfo-containing polyester is prepared. Examples of the reactive groups which X may represent include a hydroxy, carboxy, amino, alkylamino, an ester radical, an amido radical and the like. The ester radicals may be any radical having the formulae:

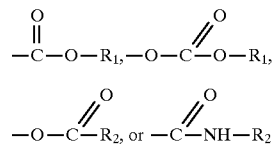

wherein $R_1$ is unsubstituted or substituted $C_1$–$C_5$ alkyl, $C_5$–$C_7$ cycloalkyl, phenyl or substituted phenyl. $R_1$ is preferably unsubstituted alkyl of up to about four carbon atoms, e.g. methyl and ethyl. $R_2$ is hydrogen or those groups listed for $R_1$. Typical substituents on the alkyl groups represented by $R_1$ and $R_2$ include hydroxy, $C_1$–$C_4$ alkoxy and halogen, phenyl, cyclohexyl, 2-furyl, furyl, cyano and halogen. Typical substituents on the phenyl groups represented by $R_1$ and $R_2$ include $C_1$–$C_4$ alkyl, $C_1$–$C_4$ alkoxy and halogen. Reactive group X preferably is hydroxy, carboxy, carbalkoxy or alkanoyloxy of up to about 4 carbon atoms, e.g. carbomethoxy or acetoxy. It is to be understood that X may represent two different reactive groups, e.g. one X group may represent hydroxy while the other X group may represent carboxy.

The aforedescribed colored polyester and polyamide material are prepared according to the technology for preparing sulfo-containing polymers as described in U.S. Pat. Nos. 3,546,008; 3,734,874; 3,779,993; 4,233,196; 4,335, 220; and, in particular, U.S. Pat. No. 4,804,719, the disclosures of which are incorporated herein by reference.

The invention also relates to a composition (I) for coloring keratinous fibers which comprises:

(1) about 0.05 to about 40 weight % of a colored, sulfo-containing, water-dispersible, polymer having about 20 mole % to about 100 mole % carbonyloxy linking groups and 0% to about 80 mole % carbonylamide linking groups, wherein the colorant moiety is reacted into or onto the backbone of the polymer; and (2) about 50 to about 99.95 weight % of a vehicle consisting of water or water/alcohol with the provision that the alcohol is a $C_2$–$C_3$ alcohol and that the alcohol content does not exceed about 55% by weight of the total weight of the hair coloring composition.

Optionally, about 0.1 to about 10 weight % of an emulsifier may also be present in the composition.

The invention also relates to a haircoloring composition (II) for coloring kertinous fibers which comprises:

(1) about 0.05 to about 40 weight % of a colored sulfo-containing, water-dispersible polymer having about 20 mole % to about 100% carbonyloxy linking groups and 0% to about 80 mole % carbonylamide linking groups and wherein the colorant moiety is reacted into or onto the backbone the polymer;

(2) about 0.05 to about 10 weight % of a nonionic hydrophobically modified associative thickener selected from the groups of such polymers described in U.S. Pat. Nos. 4,155,892 and 4,228,277 and mixtures thereof. A preferred commercially available example of a polymer of the type described in U.S. Pat. No. 4,155,892 is Aculyn 44® from Rohm and Haas Company, which is described in their technical literature as a nonionic rheology modifier based upon hydrophobically modified polyurethane chemistry. A preferred commercially available example of a polymer of the type described in U.S. Pat. No. 4,228,277 is Natrosol® Plus CS, Grade 330 from Aqualon Company, which is described in their technical literature as a nonionic water soluble modified hydroxyethylcellulose associative thickener; and (3) about 50 to about 99.90 weight % of a vehicle consisting of water or water/alcohol with the provision that the alcohol is a $C_2$–$C_3$ alcohol and that the alcohol content does not exceed about 55% by weight of the total weight of the haircoloring composition.

The invention also relates to a haircoloring composition (III) which comprises:

(1) about 0.05 to about 40 weight % of a colored sulfo-containing, water-dispersible polymer having about 20 mole % to about 100% carbonyloxy linking groups and 0% to about 80 mole % carbonylamide linking groups and wherein the colorant moiety is reacted into or onto the backbone the polymer;

(2) about 0.05 to about 10% percent of a nonionic hydrophobically modified associative thickener selected from the groups of such polymers described in U.S. Pat. Nos. 4,155,892 and 4,228,277 and mixtures thereof. A preferred commercially available example of a polymer of the type described in U.S. Pat. No. 4,155,892 is Aculyn 44® from Rohm and Haas Company, which is described in their technical literature as a nonionic rheology modifier based upon hydrophobically modified polyurethan chemistry. A preferred commercially available example of a polymer of the type described in U.S. Pat. No. 4,228,277 is Natrosol® Plus CS, Grade 330 from Aqualon Company, which is described in their technical literature as a nonionic water soluble modified hydroxyethylcellulose associative thickener;

(3) about 0.01 to about 10 weight % of one or more water soluble amphoteric, zwitterionic, nonionic or anionic surfactants; and (4) about 40 to about 99.90 weight % of a vehicle consisting of water or water/alcohol with the provision that the alcohol is a C2–C3 alcohol and that the alcohol content does not exceed about 55% by weight of the total weight of the haircoloring composition.

In the preferred embodiment of Composition III, the concentration of colored polymer would be in the range of 0.1 to about 15 weight %, the concentration of nonionic hydrophobically modified associative thickener in the range of 0.05 to about 5 weight %, and the concentration of water soluble surfactant in the range of 0 to about 3 weight %.

In a preferred embodiment of Compositions I–III above, the carbonyloxy linking groups are polyesters and the carbonylamide linking groups, if any, are polyamides.

In an alternative embodiment of hair coloring Compositions I–III above, the polymer described in (1) above may be a blend of polymers comprising:

(a) about 5 to about 100 weight %, based upon the blend of polymeric materials, of a colored, water-dispersible polymeric material having linking groups comprising about 20 mole % to about 100 mole % carbonyloxy and 0% to about 80 mole % carbonylamide, said polymeric material containing water-solubilizing sulfonate groups and having reacted into or onto the polymer backbone from about 1 to about 40 mole %, based on the total of all reactant hydroxy, carboxy and amino equivalents, and the condensable derivatives thereof, of colorant comprising one or more heat stable organic compounds initially having at least one condensable group; and (b) 0 to about 95 weight %, based upon the blend of polymeric materials, of an uncolored, water-dispersible polymeric material comprising:

(i) about 50 to about 100 weight %, based upon the total of (b), of a water-dispersible polymeric material having linking groups comprising about 20 mole % to about 100 mole % carbonyloxy and 0% to about 80 mole % carbonylamide, said polymeric material containing water-solubilizing sulfonate groups; and (ii) 0 to about 50 weight %, based upon the total of (b), of a water-soluble vinyl polymer or copolymer which contains at least about 50 mole % of the residues of a vinyl lactam monomer having Formula I:

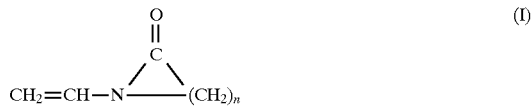

wherein n is 3 or 4;

provided said colored, water-dispersible polymeric material comprises a tinctorially effective amount of the hair coloring composition, preferably about 0.05 to about 40 weight % of the hair coloring composition.

The colorless, sulfo-containing, water-dispersible polyesters and polyamides useful in the above hair coloring formulation are described in detail in U.S. Pat. Nos. 3,546,008; 3,734,874; 3,779,993; and 4,335,220 and some compositions are commercially available from Eastman Chemical Company as Eastman AQ29D, 29S, 38D, 38S, 48D, 48S, 55D and 55S.

Vinyl monomers useful for copolymerizing with the vinyl lactams of Formula I to produce the water soluble vinyl copolymer include those of Formulae II, III and IV below:

wherein $R_3$ is selected from $C_1$–$C_{10}$ alkyl groups; $R_4$ is hydrogen or methyl; $R_5$ is $C_1$–$C_{10}$ alkyl or $C_1$–$C_{10}$ alkylene-$N(R_7)R_8$, wherein $R_7$ and $R_8$ are independently selected from hydrogen, $C_1$–$C_2$ alkyl and hydroxy $C_1$–$C_4$ alkyl; and $R_6$ is hydrogen or $C_1$–$C_6$ alkyl. Vinyl acetate, styrene, acrylate esters and methacrylate esters are typical comonomers which provide suitable water soluble vinyl copolymers for the practice of the invention.

Other additives such as preservatives, fragrances, pH adjusting agents, hair conditioners, antifoaming agents, antistatic agents, plasticizers, etc. may be added to the hair colorant formulation in such quantities as desired, usually up to about 5.0% by weight of the total composition.

Of course, aerosol propellants may be added to generate mousses, sprays, foams, etc. Preferred aerosol propellants are dimethyl ether or an aliphatic hydrocarbon component consisting of $C_1$–$C_4$ straight or branched chain hydrocarbons such as methane, ethane, propane, n-butane, isobutane, etc., or mixtures thereof.

The hair coloring compositions described herein provide surprisingly desirable non-permanent colorings of hair which are easily and completely removable in hot water, or in the presence of surfactants such as when shampooing, yet offer excellent resistance to redispersion in ambient temperature water and excellent resistance to flaking during combing and brushing. Additionally, the surprisingly balanced substantivity property results in virtually no color rub-off. Thus, a superior non-permanent hair coloring method and composition are provided.

The following examples further illustrate the practice of the invention:

EXAMPLE 1

Components (a)–(g) comprising

| | | |
|---|---|---|
| (a) | 80.3 g (0.414 m) | dimethyl isophthalate |
| (b) | 26.9 g (0.091 m) | dimethyl-5-sodiosulfoisophthalate |
| (c) | 54.1 g (0.51 m) | diethylene glycol |
| (d) | 37.4 g (0.26 m) | 1,4-cyclohexanedimethanol |
| (e) | 0.75 g (.0091 m) | anhydrous sodium acetate |
| (f) | 100 ppm | Ti catalyst as titanium tetraisopropoxide |
| (g) | 15.0 g (.0181 m) | cyan colorant having the formula CuPc[$SO_2NHCH_2C(CH_3)_2CH_2OH$]$_{2.5}$ |

Pc = phthalocyanine nucleus were added to a 500 mL round bottom flask that was fitted with a stirrer, condensate take off, and nitrogen inlet head. The flask and contents were immersed into a Belmont metal bath and heated for two hours at 200°–220° C. while ester interchange occurred. To carry out the polycondensation reaction, the temperature was increased to about 250° C. and the flask was held under vacuum ≦0.5 mmHg for about 20 minutes. The resulting polymer was dark blue and contained about 10% (W/W) cyan colorant. The polymer was granulated by grinding in a Wiley mill. It has a weight average molecular weight of 12,027 and a number average molecular weight of 4,393 by gel permeation phase chromatography (GPC) and a polydispersity value of 2.73.

EXAMPLE 2

A portion (60.0 g) of the sulfo-containing polymeric colorant of Example 1 was added portionwise to water (180 g) and the mixture stirred at the boil, allowing some of the water to evaporate, for about 10 minutes to give a dark cyan solution. The total weight was about 200 g, thus giving a 30% by weight solution of the colorant in water.

EXAMPLE 3

Example 1 was repeated using 15.0 g (0.02 m) of magenta colorant

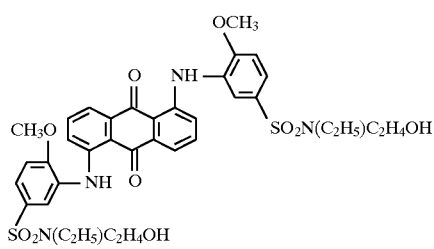

to replace component (g) to produce a dark red polymer which contains about 10% by weight of the magenta colorant and which as an I.V. of 0.24, a Tg at 60.1° C., a weight average molecular weight of 13,979, a number average molecular weight of 5,222 and a polydispersity value of 2.67.

EXAMPLE 4

A portion of the sulfo-containing polyester colorant of Example 3 (60.0 g) was added portionwise to water (180 g) to prepare about a 30% by weight aqueous magenta solution of the colorant, as described in the method of Example 2.

EXAMPLE 5

Example 1 was repeated using 15.0 g (0.045 m) of yellow colorant

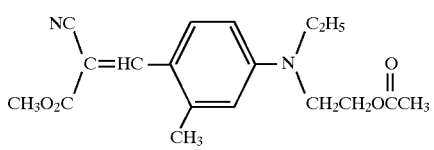

to replace component (g) to produce a dark yellow polymer which contains about 10% by weight of yellow colorant and which has an I.V. of 0.23, a Tg at 56.1° C., a weight average molecular weight of 12,476, a number average molecular weight of 4,224 and a polydispersity of 2.95.

EXAMPLE 6

A portion of the sulfo-containing polyester colorant of Example 5 (60.0 g) was added to water to prepare a 30% by weight aqueous yellow solution, as described in the method of Example 2.

EXAMPLE 7

Example 1 was repeated using 15.0 g (0.037 m) of red colorant

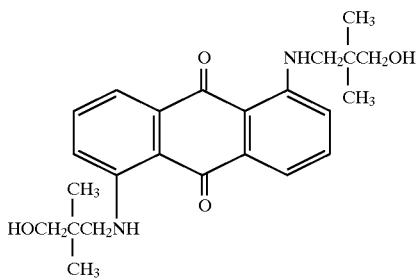

to replace component (g) to produce a dark red polymer which contains about 10% by weight of the red colorant and which has an I.V. of 0.235, a Tg at 57.51° C., a weight average molecular weight of 12,728, a number average molecular weight of 5,035 and a polydispersity value of 2.53.

EXAMPLE 8

A portion of the sulfo-containing polyester colorant of Example 7 (60.0 g) was added to water to prepare a 30% by weight aqueous red solution, as described in the method of Example 2.

EXAMPLE 9

The procedure of Example 1 was repeated using (a) 67.1 g (0.35 m) dimethyl isophthalate (b) 20.3 g (0.07 m) dimethyl-5-sodiosulfoisophthalate (c) 31.4 g (0.30 m) diethylene glycol (d) 28.0 g (0.19 m) 1,4-cyclohexanedimethanol (e) 0.75 g (0.009 m) anhydrous sodium acetate (f) 28.0 g (0.068 m) colorant used in Example 7 to produce a sulfo-containing polyester red colorant which contains about 20% by weight of the red anthraquinone colorant and which has an I.V. of 0.30, a Tg at 70.2° C., a weight average molecular weight of 13,889, a number average molecular weight of 7,110 and a polydispersity value of 1.95.

EXAMPLE 10

The procedure of Example 1 was repeated using (a) 59.4 g (0.81 m) dimethyl isophthalate (b) 18.0 g (0.06 m) dimethyl-5-sodiosulfoisophthalate (c) 25.7 g (0.24 m) diethylene glycol (d) 24.8 g (0.17 m) 1,4-cyclohexanedimethanol (e) 0.75 g (0.009 m) anhydrous sodium acetate (f) 42.0 g (0.10 m) colorant used in Example 7 to produce a sulfo-containing polyester red colorant which contains about 30% by weight of the red anthraquinone colorant and which as an I.V. of 0.22, a Tg of 83.3° C., a weight average molecular weight of 12,436, a number average molecular weight of 6,270 and a polydispersity value of 2.0.

EXAMPLE 11

The procedure of Example 1 was repeated using (a) 51.5 g (0.27 m) dimethyl isophthalate (b) 15.6 g (0.50 m) dimethyl-5-sodiosulfoisophthalate (c) 20.5 g (0.19 m) diethylene glycol (d) 21.5 g (0.15 m) 1,4-cyclohexanedimethanol (e) 0.75 g (0.009 m) anhydrous sodium acetate (f) 56.0 g (0.136 m) colorant used in Example 7 to produce a sulfo-containing polyester red colorant which contains about 40% by weight of the red anthraquinone colorant and which has an I.V. of 0.25, a Tg of 94.9° C., a weight average molecular weight of 10,635, a number average molecular weight of 5,846 and a polydispersity value of 1.82.

EXAMPLE 12

The procedure of Example 1 was repeated using (a) 40.5 g (0.22 m) dimethyl isophthalate (b) 13.2 g (0.04 m) dimethyl-5-sodiosulfoisophthalate (c) 15.7 g (0.15 m) diethylene glycol (d) 18.1 g (0.13 m) 1,4-cyclohexanedimethanol (e) 0.75 g (0.009 m) anhydrous sodium acetate (f) 70.0 g (0.170 m) colorant used in Example 7 to produce a sulfo-containing polyester red colorant which contains about 50% by weight of the red anthraquinone colorant and which as an I.V. of 0.155, a Tg at 108° C., a weight average molecular weight of 8,032, a number average molecular weight of 4,442 and a polydispersity value of 1.81.

EXAMPLE 13

Example 1 was repeated using 15.0 g (0.0187 m) of blue colorant

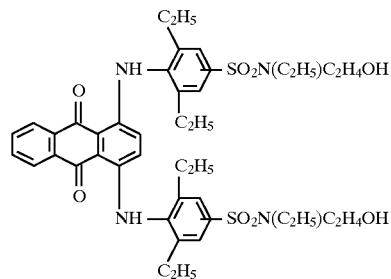

to replace component (g) to produce a dark blue polymer which contains about 10% by weight of the blue anthraquinone colorant and which has an I.V. of 0.30, a Tg at 64.4° C., a weight average molecular weight of 15,850, a number average molecular weight of 5,163 and a polydispersity value of 3.07.

EXAMPLE 14

A portion of the sulfo-containing polyester of Example 13 (60.0 g) was added to water to prepare a 30% weight aqueous blue solution, as described in the method of Example 2.

EXAMPLE 15

Example 1 was repeated using 15.0 g (0.031M) of red colorant

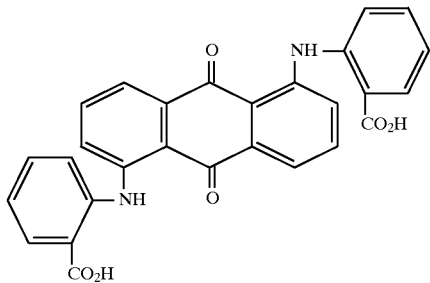

to replace component (g) to produce a dark red polymer which contains about 10% by weight of the red anthraquinone colorant and which has an I.V. of 0.207, a Tg at 56.9°, a weight average molecular weight of 12,724, a number average molecular weight of 4,189 and a polydispersity value of 3.01.

EXAMPLE 16

A portion (60.0 g) of the sulfo-containing polyester colorant of Example 15 was added to water to prepare a 30% by weight aqueous magenta solution, as described in the method of Example 2.

EXAMPLE 17

Example 1 was repeated using 15.0 g (0.028 m) of red colorant

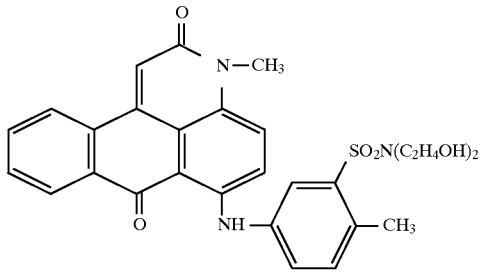

to replace component (g) to produce a dark red polymer which contains about 10% by weight of the red anthrapyridone colorant and which has an I.V. of 0.22, a Tg at 61.9° C., a weight average molecular weight of 11,621, a number average molecular weight of 4,021 and a polydispersity value of 2.89.

EXAMPLE 18

A portion (60.0 g) of the sulfo-containing polyester of Example 17 was added to water to prepare a 30% by weight aqueous red solution, as described in the method of Example 2.

EXAMPLE 19

A portion (110 g) of the sulfo-containing polyester colorant of Example 10 was added portionwise to boiling water (275 mL). Heat was lowered somewhat and stirring continued to complete solution. Adjusted total weight to 366 g, thus giving a 30% by weight aqueous solution of the polymer. After standing overnight, a gel-like solid had formed in the bottom of the container. The material was diluted with stirring to produce a total weight of 671 g, thus providing a 16% by weight solution of the colored polyester in water.

EXAMPLE 20

Components (a)–(f) comprising
- (a) 87.4 g (0.45 m) dimethyl isophthalate
- (b) 14.9 g (0.05 m) dimethyl 5-sodiosulfoisophthalate
- (c) 82.1 g (0.77 m) diethylene glycol
- (d) 0.41 g (0.005 m) anhydrous sodium acetate
- (e) 100 ppm Ti catalyst as titanium tetraisopropoxide
- (f) 14.0 g (0.0186 m) magenta colorant used in Example 3 were added to a 500 mL round bottom flask that was fitted with a stirrer, condensate take off and nitrogen inlet head. The flask and contents were immersed into a Belmont metal bath and heated for 1 hr. at 200° C. The temperature was increased to 230° C. and maintained for 90 minutes while ester interchange occurred. To carry out the polycondensation, the temperature was increased to 270° C. and held for 15 minutes. The pressure was then gradually reduced to about ≦0.5mmHg over about a 10-minute period and then the temperature was held for about 30 minutes. The resulting polymer was dark red and contained about 10% (w/w) of magenta colorant. The polymer was granulated by grinding in a Wiley mill. It has an I.V. of 0.36, a Tg at 36.4° C., a weight average molecular weight of 22,995, a number average molecular weight of 10,107 and a polydispersity value of 2.28.

EXAMPLE 21

A 30% by weight solution of the sulfo-containing polymeric colorant of Example 20 was prepared by dissolving 110 g of the colored polymer in water (275 mL) and boiling to facilitate solution and then adjusting the amount of water needed.

EXAMPLE 22

Components (a)–(g) comprising
- (a) 84.5 g (0.44 m) dimethyl isophthalate
- (b) 14.4 g (0.05 m) dimethyl sodiosulfoisophthalate
- (c) 62.4 g (0.59 m) diethylene glycol
- (d) 15.5 g (0.11 m) 1,4-cyclohexanedimethanol
- (e) 6.40 g (0.0049) m anhydrous sodium acetate
- (f) 100 ppm Ti catalyst as titanium tetraisopropoxide
- (g) 14.0 g (0.0186 m) magenta colorant used in Example 3 were reacted exactly as described in Example 20 to give a sulfo-polyester polymer containing about 10% (w/w) of the magenta colorant. The polymer has an I.V. of 0.38, a Tg at 45.2° C., a weight average molecular weight of 24,477, a number average molecular weight of 10,612 and a polydispersity value of 2.5.

EXAMPLE 23

A portion (100 g) of the sulfo-containing polyester of Example 22 was dissolved in water (250 mL) by stirring and heating at the boiling point and then the amount of water adjusted to give a 28% by weight aqueous solution of polymer in water.

EXAMPLE 24

A blend of sulfo-containing polyester colorants was prepared by combining the solutions as prepared in Example 2 (4.0 g), Example 4 (2.0 g), Example 6 (2.0 g) and Example 8 (0.80 g) by stirring together.

EXAMPLE 25

Eight grams of Eastman AQ55S, a sulfo-containing, water dispersible polymer from Eastman Chemical Company, was added with stirring to water at 80°–85° C. and the mixture stirred until the polymer was completely dispersed in water. After cooling, a sufficient quantity of preservative was added. MYVATEX Texture Lite (5.5 g), an emulsifier supplied by Eastman Chemical Company, was added with high-speed agitation, being careful to avoid aeration. When the mixture was uniform, MYVATEX 60 (0.8 g), an emulsifier from Eastman Chemical Company, and MONAMID 150 ADD (1.0 g), a foam stabilizer from Mona, were added. A desired amount of fragrance was added and the pH of the formulation was adjusted to 6.5–7.0 by addition of citric acid.

EXAMPLE 26

A portion (20.0 g) of the basic mousse formulation of Example 25 was combined with the mixture of sulfo-containing polyester colorants of Example 24 by mixing and the mixture combined with 5.0 g of A46 propellant, a dimethyl ether aerosol propellant from Aeropress.

EXAMPLE 27

The aerosol hair coloration formulation of Example 26 was applied to uncolored hair tresses by spraying at room temperature. After a few minutes, some of the tresses were rinsed by holding under cold running tap water. Other tresses were allowed to dry overnight and then rinsed by holding under hot tap water. All of the samples showed good coverage and considerable color. Shampooing and then rinsing of the colored hair tresses with warm tap water removed most of the coloration. Thus, a method of providing temporary hair coloration which is readily removed by shampooing is provided.

EXAMPLE 28

Color Refresher

| | Weight of polymer solution and of other ingredients | % Weight of polymer in final composition |
| --- | --- | --- |
| Yellow Methine (30 WT % aqueous colored polymer solution). (Ex. 6) | 5.0 g | 1.5 |
| Red Anthrapyridone (30 WT % aqueous colored polymer solution). (Ex. 18) | 1.6 g | 0.48 |
| Blue Anthraquinone (30 WT % aqueous colored polymer solution). (Ex. 14) | .5 g | 0.15 |
| Triton X-100 nonionic surfactant. Dow Corning | 0.2 g | |
| Deionized water | 92.7 g | |

The colored polymer solutions were combined with the surfactant and deionized water by stirring at room temperature. The composition was applied to naturally blonde hair tresses by wetting the fibers, removing excess composition with towel, and blow drying. It produced a golden reddish shade. The hair showed no flaking when brushed, no color rub-off against a white cloth, and insignificant color bleed in tap water. We normally observe less color bleed in tap water than in distilled or deionized water. Consequently, bleeding in deionized water is a more stringent test for resistance to color bleeding (see EXAMPLES 36, 37, and 48–56). The color on hair was completely removable by lathering with a commercial shampoo. The composition was especially useful as a color refresher to adjust for fading on hair previously colored with a permanent oxidation dye product.

EXAMPLE 29

Color Refresher

| | Weight of polymer solution and of other ingredients | % Weight of polymer in final composition |
| --- | --- | --- |
| Yellow Methine (30 WT % aqueous colored polymer solution). (Ex. 6) | 3.0 g | 0.9 |
| Red Anthrapyridone (30 WT % aqueous colored polymer solution). (Ex. 18) | 2.4 g | 0.72 |
| Blue Anthraquinone (30 WT % aqueous colored polymer solution). (Ex. 14) | 0.12 g | 0.036 |
| Triton X-100 nonionic surfactant. Dow Corning | 0.2 g | |
| Deionized water | 94.28 g | |

The colored polymer solutions were combined with the surfactant and deionized water by stirring at room temperature. The composition was applied to naturally blonde hair tresses as described in Example 28, producing a reddish orange shade. Other comments under Example 28 equally apply.

EXAMPLE 30

Color Refresher

| | Weight of polymer solution and of other ingredients | % Weight of polymer in final composition |
| --- | --- | --- |
| CyanCuPc (30 WT % aqueous colored polymer solution). (Ex. 2) | 4.0 g | 1.2 |
| Magenta Anthraquinone (30 WT % aqueous colored polymer solution). (Ex. 4) | 9.0 g | 2.61 |
| Triton X-100 nonionic surfactant. Dow Corning | .2 g | |
| Deionized water | 86.8 g | |

The colored polymer solutions were combined with the surfactant and deionized water by stirring at room temperature. The composition was applied to naturally blonde hair tresses as described in Example 28, producing a smoky grey shade. Other comments under Example 28 equally apply.

EXAMPLE 31

Color Refresher

| | Weight of polymer solution and of other ingredients | % Weight of polymer in final composition |
| --- | --- | --- |
| Yellow Methine (30 WT % aqueous colored polymer solution). (Ex. 6) | 0.5 g | 0.15 |
| Red Anthrapyridone (30 WT % aqueous colored polymer solution). (Ex. 18) | 1.6 g | 0.48 |
| Blue Anthraquinone (30 WT % aqueous colored polymer solution). (Ex. 14) | 0.2 g | 0.06 |
| Triton X-100 nonionic surfactant. Dow Corning | 0.2 g | |
| Deionized water | 86.8 g | |

The colored polymer solutions were combined with the surfactant and deionized water by stirring at room temperature. The composition was applied to naturally blonde hair tresses as described in Example 28, producing a reddish orange shade. Other comments under Example 28 equally apply.

EXAMPLE 32

Color Refresher with Hair Setting Properties

| | Weight of polymer solution and of other ingredients | % Weight of polymer in final composition |
| --- | --- | --- |
| CyanCuPc (30 WT % aqueous colored polymer solution). (Ex. 2) | 1.0 g | 0.3 |

Color Refresher with Hair Setting Properties

| | Weight of polymer solution and of other ingredients | % Weight of polymer in final composition |
|---|---|---|
| Magenta Anthraquinone (30 WT % aqueous colored polymer solution). (Ex. 4) | 2.25 g | 0.675 |
| Blue Anthraquinone (30 WT % aqueous colored polymer solution). (Ex. 14) | .33 g | 0.099 |
| Triton X-100 nonionic surfactant. Dow Corning | .2 g | |
| Eastman AQ55S sulfo-containing water dispersible solid polyester polymer. (Eastman Chem. Co.) | 10.0 g | 10.0 |
| Deionized water | 86.22 g | |

In a first step, 10 g of Eastman AQ55S polymer were added with stirring to 86.22 g of water at 80°–85° C. and the mixture stirred until the polymer was completely dispersed in water. After cooling, this solution was added to the colored polymer solutions and surfactant and mixed by stirring at room temperature. The composition was applied to naturally blonde hair tresses by spreading it with the fingers. The tresses were then wound on half-inch diameter rollers and blow dried. After removal from the rollers, the hair tresses retained the curled configuration for 10 hours at 65% R.H. The composition imparted a light grey color to the hair. The hair showed very little flaking when brushed, no color rub-off against a white cloth, and insignificant color bleed in tap water. The color on hair was completely removable by lathering with a commercial shampoo. The composition can be advantageously used as a color refresher with hair setting action.

EXAMPLE 33

Color Refresher with Soft Natural Feel

| | Weight of polymer solution and of other ingredients | % Weight of polymer in final composition |
|---|---|---|
| Yellow Methine (30 WT % aqueous colored polymer solution). (Ex. 6) | 0.1 g | 0.03 |
| Red Anthraquinone (16 WT % aqueous colored polymer solution). (Ex. 19) | 1.0 g | .16 |
| Blue Anthraquinone (30 WT % aqueous colored polymer solution). (Ex. 14) | 0.1 g | 0.03 |
| Triton X-100 nonionic surfactant. Dow Corning | 0.2 g | |
| Deionized water | 98.6 g | |

The colored polymer solutions were combined with the surfactant and deionized water by stirring at room temperature. The composition was applied to naturally blonde hair tresses as described in Example 28, producing a pale reddish shade. The composition can be used as a color refresher to adjust for fading on hair previously colored with a permanent oxidation dye product. In addition, the natural feel of the hair remains practically unaffected because Red Anthraquinone, the major component, contains a very high level of chromophore (30 WT %) in its backbone and not much of it is needed to produce useful shades. Polymers used in Examples 24–32 have only 10 WT % of chromophore in the backbone.

EXAMPLE 34

Color Refresher with Soft Natural Feel

| | Weight of polymer solution and of other ingredients | % Weight of polymer in final composition |
|---|---|---|
| Yellow Methine (30 WT % aqueous colored polymer solution). (Ex. 6) | 0.2 g | 0.06 |
| Red Anthraquinone (16 WT % aqueous colored polymer solution). (Ex. 19) | 1.5 g | 0.24 |
| Blue Anthraquinone (30 WT % aqueous colored polymer solution). (Ex. 14) | 0.2 g | 0.06 |
| Triton X-100 nonionic surfactant. Dow Corning | 0.2 g | |
| Deionized water | 97.9 g | |

The colored polymer solutions were combined with the surfactant and the deionized water by stirring at room temperature. The composition was applied to naturally blonde hair tresses as described in Example 28, producing a reddish shade. The composition can be used as a color refresher to adjust for fading of hair previously colored with a permanent oxidation dye product. As in Example 33 the Red Anthraquinone allows, if it is desired, to formulate color refreshers which have negligible effects on the original feel of the hair.

EXAMPLE 35

Color Refresher with Conditioning Properties

| | Weight of polymer solution and of other ingredients | % Weight of polymer in final composition |
|---|---|---|
| CyanCuPc (30 WT % aqueous colored polymer solution). (Ex. 2) | 2.0 g | 0.6 |
| Magenta Anthraquinone (30 WT % aqueous colored polymer solution). (Ex. 4) | 4.5 g | 1.35 |
| Q2-7224 Silicone Emulsion. Dow Corning | 2.0 g | |
| Triton X-100 nonionic surfactant. Dow Corning | 0.2 g | |
| Deionized water | 91.3 g | |

The colored polymer solutions were combined with the other ingredients by stirring at room temperature. The composition was applied to naturally blonde hair tresses as described in Example 28, producing a violet shade. The hair showed no flaking when brushed, very small level of rub-off against a white cloth and insignificant color bleed in tap water. The color is completely removable by shampooing. The composition can be used as a color refresher. The incorporation of the silicone emulsion into the composition makes the hair very easy to comb during and after product application. It also confers a soft silky feel to the treated hair.

EXAMPLE 36

Color Refresher with Excellent Resistance to Color Bleed

| | Weight of polymer solution and of other ingredients | % Weight of polymer in final composition |
|---|---|---|
| Yellow Methine (30 WT % aqueous colored polymer solution). (Ex. 6) | 0.5 g | 0.15 |
| Magenta Anthraquinone (30 WT % aqueous colored polymer solution). (Ex. 21) | 1.5 g | 0.45 |
| Triton X-100 nonionic surfactant. Dow Corning | 0.2 g | |
| Deionized water | 97.8 g | |

The colored polymer solutions were combined with the surfactant and the deionized water by stirring at room temperature. The composition was applied to naturally blonde hair tresses as described in Example 28, producing a golden blonde shade. The use of Magenta Anthraquinone, which has a low glass transition temp (36.4° C.), makes this composition very resistant to color bleed even in very pure deionized water, without introducing negative performance effects. Colored polymers used in examples 24 through 35 have glass transition temperatures higher than 55° C.

EXAMPLE 37

Color Refresher with Excellent Resistance to Color Bleed

| | Weight of polymer solution and of other ingredients | % Weight of polymer in final composition |
|---|---|---|
| Yellow Methine (30 WT % aqueous colored polymer solution). (Ex. 6) | 1.0 g | 0.30 |
| Magenta Anthraquinone (28 WT % aqueous colored polymer solution). (Ex. 23) | 5.0 g | 1.5 |
| Triton X-100 nonionic surfactant. Dow Corning | .2 g | |
| Deionized water | 93.8 g | |

The colored polymer solutions were combined with the surfactant and the deionized water by stirring at room temperature. The composition was applied to naturally blonde hair tresses as described in Example 28, producing a reddish golden shade. As in Example 36, the use of Magenta Anthraquinone, which also has a low glass transition temperature (45.2° C.), produces excellent resistance to color bleed even in very pure deionized water, without introducing any negative performance effects.

EXAMPLE 38

Temporary Hair Colorant

| | Weight of polymer solution and of other ingredients | % Weight of polymer in final composition |
|---|---|---|
| Yellow Methine (30 WT % aqueous colored polymer solution). (Ex. 6) | 10.0 g | 3.0 |
| CyanCuPc (30 WT % aqueous colored polymer solution). (Ex. 2) | 20.0 g | 6.0 |
| Red Anthraquinone (30 WT % aqueous colored polymer solution). (Ex. 16) | 55.0 g | 16.5 |
| Triton X-100 nonionic surfactant. Dow Corning | 0.2 g | |
| Deionized water | 14.8 g | |

The colored polymer solutions were combined with the surfactant and the deionized water by stirring at room temperature. The composition was applied to natural grey hair tresses by wetting the fibers, removing excess composition with towel and blow drying. It produced a medium black color on the hair. The hair showed very small level of flaking when brushed, slight rub-off when rubbed against a white cloth and insignificant color bleed in tap water. The color on hair was completely removed by lathering with a commercial shampoo. The composition can be used as a temporary hair coloring treatment to produce very significant changes in the original color of hair. Due to the high level of colored polymer in the composition, the treatment is an excellent setting agent for hair.

EXAMPLE 39

Temporary Hair Colorant

| | Weight of polymer solution and of other ingredients | % Weight of polymer in final composition |
|---|---|---|
| Yellow Methine (30 WT % aqueous colored polymer solution). (Ex. 6) | 15.0 g | 4.5 |
| Red Anthraquinone (30 WT % aqueous colored polymer solution). (Ex. 16) | 5.0 g | 1.5 |
| Blue Anthraquinone (30 WT % aqueous colored polymer solution). (Ex. 14) | 2.6 g | 0.78 |
| Triton X-100 nonionic surfactant. Dow Corning | 0.2 g | |
| Deionized water | 77.2 g | |

The colored polymer solutions were combined with the surfactant and the deionized water by stirring at room temperature. The composition was applied to naturally blonde hair tresses as described in Example 38. It produced a medium golden brown shade. Other comments under Example 38 equally apply.

EXAMPLE 40

Temporary Hair Colorant

| | Weight of polymer solution and of other ingredients | % Weight of polymer in final composition |
|---|---|---|
| Yellow Methine (30 WT % aqueous colored polymer solution). (Ex. 6) | 15.0 g | 4.5 |
| Red Anthraquinone (30 WT % aqueous colored polymer solution). (Ex. 16) | 8.0 g | 2.4 |

EXAMPLE 40 -continued

Temporary Hair Colorant

| | Weight of polymer solution and of other ingredients | % Weight of polymer in final composition |
|---|---|---|
| Blue Anthraquinone (30 WT % aqueous colored polymer solution). (Ex. 14) | 1.5 g | 0.45 |
| Triton X-100 nonionic surfactant. Dow Corning | 0.2 g | |
| Deionized water | 75.3 g | |

The colored polymer solutions were combined with the surfactant and the deionized water by stirring at room temperature. The composition was applied to natural grey hair as described in Example 38. It produced a reddish brown shade. Other comments under Example 38 equally apply.

EXAMPLE 41

Temporary Hair Colorant

| | Weight of polymer solution and of other ingredients | % Weight of polymer in final composition |
|---|---|---|
| Yellow Methine (30 WT % aqueous colored polymer solution). (Ex. 6) | 15.0 g | 4.5 |
| Red Anthraquinone (30 WT % aqueous colored polymer solution). (Ex. 16) | 12.0 g | 3.6 |
| Blue Anthraquinone (30 WT % aqueous colored polymer solution). (Ex. 14) | 0.6 g | 0.18 |
| Triton X-100 nonionic surfactant. Dow Corning | 0.2 g | |
| Deionized water | 72.2 g | |

The colored polymer solutions were combined with the surfactant and the deionized water by stirring at room temperature. The composition was applied to natural grey hair as described in Example 38. It produced an auburn shade. Other comments under Example 38 equally apply.

EXAMPLE 42

Temporary Hair Colorant Made Durable by After Treatment

| | Weight of polymer solution and of other ingredients | % Weight of polymer in final composition |
|---|---|---|
| Yellow Methine (30 WT % aqueous colored polymer solution). (Ex. 6) | 15.0 g | 4.5 |
| Red Anthraquinone (30 WT % aqueous colored polymer solution). (Ex. 16) | 8.0 g | 2.32 |
| Blue Anthraquinone (30 WT % aqueous colored polymer solution). (Ex. 14) | 1.0 g | 0.3 |
| Triton X-100 nonionic surfactant. Dow Corning | 0.2 g | |
| Deionized water | 75.8 g | |

The colored polymer solutions were combined with the surfactant and the deionized water by stirring at room temperature. The composition was applied to naturally blonde hair tresses as described in Example 28. It produced a reddish brown color. The hair showed very small level of flaking when brushed, slight rub-off against a white cloth, and insignificant color bleed in tap water. As in previous examples, if the tresses are shampooed at this stage, all of the color from the hair can be removed by one or at the most two latherings with a commercial shampoo. If on the other hand the colored hair tresses are then treated by quick immersion in a 3.0% aqueous solution of Ferric Chloride ($FeCl_3.6H_2O$) and dried, one observes that after six latherings with a commercial shampoo a considerable amount of color still remains on the hair. Even after six additional latherings, for a total of twelve, the original reddish brown color is still perceptible, albeit much weaker on the hair. An important result is that the original shade is removed on tone, that is, each of the individual colored polymers in the composition is being removed by repeated shampooing at a similar rate. This post treatment with an inorganic salt can be advantageously used to make treatments with the colored polymer in this invention more durable.

EXAMPLE 43

Non-Permanent Hair Colorant with Hair Conditioning Action

| | Weight of polymer solution and of other ingredients | % Weight of polymer in final composition |
|---|---|---|
| Yellow Methine (30 WT % aqueous colored polymer solution). (Ex. 6) | 15.0 g | 4.5 |
| Red Anthraquinone (30 WT % aqueous colored polymer solution). (Ex. 16) | 8.0 g | 2.3 |
| Blue Anthraquinone (30 WT % aqueous colored polymer solution). (Ex. 14) | 1.0 g | 0.3 |
| Q2-7224 Silicone Emulsion. Dow Corning | 6.0 | |
| Triton X-100 nonionic surfactant. Dow Corning | .2 g | |

All of the ingredients are combined by stirring at room temperature. The composition was applied to naturally blonde hair tresses, as described in Example 28. It produced an orange golden color. The hair showed no flaking when brushed, low level of rub-off against a white cloth and insignificant color bleed in tap water. The color is completely removable by shampooing. The incorporation of the silicone emulsion into the composition makes the hair very easy to comb during and after product application. It also confers a soft feel to the colored hair.

EXAMPLE 44

Example 1 was repeated using (a) 51.6 g (0.27 m) dimethyl isophthalate (b) 24.9 g (0.084 m) dimethyl-5-sodiosulfoisophthalate (c) 58.3 g (0.55 m) diethylene glycol (d) 11.4 g (0.079 m) 1,4-cyclohexanedimethanol (e) 0.75 g (0.009 m) anhydrous sodium acetate (f) 14.0 g (0.0273 m) yellow anthraquinone colorant having the formula

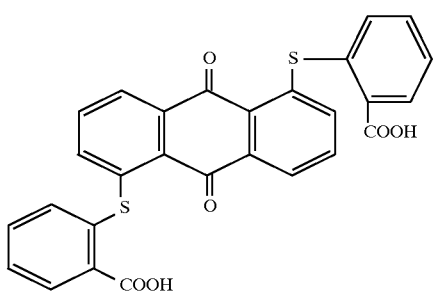

to produce a sulfo-containing polyester yellow colorant which contains about 14% by weight of the yellow anthraquinone colorant and which has a I.V. of 0.22, a Tg. of 52.3° C., a weight average molecular weight of 12,817, a number average molecular weight of 4,234 and a polydispersity of 3.0.

EXAMPLE 45

A portion of the sulfo-containing polyester of Example 44 (90 g) was added to water to prepare a 30% by weight aqueous yellow solution, as described in the method of Example 2.

EXAMPLE 46

Non-Permanent Hair Colorant with Hair Lightening Effect

|  | Weight of polymer solution and of other ingredients | % Weight of polymer in final composition |
|---|---|---|
| Yellow Anthraquinone (30 WT % aqueous colored polymer solution). (Ex. 45) | 10.0 g | 3.0 |
| Triton X-100 nonionic surfactant. Dow Corning | 0.2 g |  |
| Deionized water | 89.8 g |  |

The colored polymer solution was combined with the surfactant and the deionized water by stirring at room temperature. The composition was applied to naturally light brown hair tresses, as described in Example 38. When the treated tresses were compared to untreated controls, they were clearly lighter. The hair showed no flaking when brushed, and low level of rub-off against a white cloth. This composition illustrates how the yellow colored polymer can be used to make hair appear lighter.

EXAMPLE 47

Comparative Example

PolyT from Dynapol Corporation is a colored, sulfo-containing, water-dispersible polymer having a poly (vinyl amine) backbone (i.e. hydrocarbon chain) in which more than 90% of the available amine sites have been reacted with a yellow azo chromophore as described in U.S. Pat. Nos. 4,051,138; 4,144,252, and 4,169,203 assigned to Dynapol.

Grey and bleached hair swatches were dipped into one percent aqueous solution of PolyT, combed through, and dried at ambient conditions. The colored tresses were immersed in ambient temperature tap water for five minutes for an evaluation of water bleed. It was estimated that after this time, 95% of the color was lost from the grey hair tresses and virtually all the color was lost from the bleached hair tresses.

EXAMPLE 48

Temporary Hair Colorant

|  | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 8) | 5.0 g | 1.5 |
| Blue Anthraquinone (30 WT % aqueous colored polymer solution). (Ex. 14) | 2.6 g | 0.78 |
| Natrosol ® Plus CS Grade 330 (Aqualon) | 1.5 g |  |
| Deionized water | 75.9 g |  |

A solution of Natrosol® Plus CS was prepared by combining 1.5 g of the nonionic hydrophobically modified associative thickener with 75.9 g of deionized water and allowing it to hydrate by stirring at room temperature for 2 hours. The colored polymer solutions were then combined with the thickener solution by stirring at room temperature. The composition had a viscosity of 532 cP as measured with a Brookfield RVDV-III at 100 rpm. In the absence of Natrosol® Plus CS, the viscosity of the composition described above was 3 cP when measured under the same conditions. The composition was applied to naturally blonde hair as described in Example 38. It produced a medium reddish brown shade. It was noticed during application that the solution was easy to apply, would cling to the hair and would not drip from it. The hair showed only a very small level of flaking when brushed, and only very slight rub-off when rubbed against a white cloth. An insignificant amount of color bleed was observed when the dyed hair was immersed in deionized water at room temperature for 10 minutes. The color on the hair was completely removed by lathering with a commercial shampoo.

EXAMPLE 49

Temporary Hair Colorant

|  | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 8) | 5.0 g | 1.5 |
| Blue Anthraquinone (30 WT % aqueous colored polymer solution). (Ex. 14) | 2.6 g | 0.78 |
| Natrosol ® Plus CS Grade 330 (Aqualon) | 1.5 g |  |
| Sodium Lauryl Sulfate | 0.2 g |  |
| Deionized water | 75.7 g |  |

A solution of Natrosol® Plus CS was prepared by combining 1.5 g of the nonionic hydrophobically modified associative thickener with 75.7 g of deionized water and allowing it to hydrate by stirring at room temperature for 2 hours. The sodium lauryl sulfate and the colored polymer solutions were then combined with the thickener solution by stirring at room temperature. The composition had a viscosity of 1750 cP as measured with a Brookfield RVDV-III at 100 rpm. In the absense of Natrosol® Plus CS and sodium lauryl sulfate, the viscosity of the composition described above was 3 cP when measured under the same conditions. The composition was applied to naturally blonde hair as described in Example 38. It produced a medium reddish brown shade. Other comments under Example 48 equally apply.

EXAMPLE 50

Temporary Hair Colorant

|  | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 8) | 5.0 g | 1.5 |
| Blue Anthraquinone (30 WT % aqueous colored polymer solution). (Ex. 14) | 2.6 g | 0.78 |
| Natrosol ® Plus CS Grade 330 (Aqualon) | 1.5 g |  |
| Triton X-100 nonionic surfactant, Rohm and Haas | 0.1 g |  |
| Deionized water | 75.8 g |  |

A solution of Natrosol® Plus CS was prepared by combining 1.5 g of the nonionic hydrophobically modified associative thickener with 75.8 g of deionized water and allowing it to hydrate by stirring at room temperature for 2 hours. The Triton X-100 and the colored polymer solutions were then combined with the thickener solution by stirring at room temperature. The composition had a viscosity of 2320 cP as measured with a Brookfield RVDV-III at 100 rpm. In the absence of Natrosol® Plus CS and Triton X-100, the viscosity of the composition described above was 3 cP when measured under the same conditions. The composition was applied to naturally blonde hair as described in Example 38. It produced a medium reddish brown shade. Other comments under Example 48 equally apply.

EXAMPLE 51

Temporary Hair Colorant

|  | Weight of polymer solution and of other ingredients | % Weight of polymer in final composition |
|---|---|---|
| Yellow Anthraquinone (30 WT % aqueous colored polymer solution). (Ex. 45) | 22.0 g | 6.6 |
| Red Anthraquinone (30 WT % aqueous colored polymer solution). (Ex. 8) | 8.0 g | 2.4 |
| Blue Anthraquinone (30 WT % aqueous colored polymer solution). (Ex. 14) | 10.0 g | 3.0 |
| Natrosol ® Plus CS Grade 330 (Aqualon) | 3.0 g |  |
| Deionized water | 57.0 g |  |

A solution of Natrosol® Plus CS was prepared by combining 3.0 g of the nonionic hydrophobically modified associative thickener with 57 g of deionized water and allowing it to hydrate by stirring at room temperature for 2 hours. The colored polymer solutions were then combined with the thickener solution by stirring at room temperature. The composition had a viscosity of 11,700 cP as measured with a Brookfield RVDV-III at 100 rpm. In the absense of Natrosol® Plus CS, the viscosity of the composition described above was 4 cP when measured under the same conditions. The composition was applied to naturally gray hair as described in Example 38. It produced a medium black shade. The high viscosity of this composition makes it especially useful for application around the hair line, when spreading of the product to other parts of the scalp is not desired. The hair showed only a very small level of flaking when brushed, only very slight rub-off when rubbed against a white cloth and insignificant color bleed when immersed in deionized water at room temperature for 10 minutes. The color on the hair was completely removed by lathering with a commercial shampoo.

EXAMPLE 52

Temporary Hair Colorant

|  | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 8) | 5.0 g | 1.5 |
| Blue Anthraquinone (30 WT % aqueous colored polymer solution). (Ex. 14) | 2.6 g | 0.78 |
| Aculyn ® 44 (35 WT %, propylene glycol 60%-water 40% solution) Rohm and Haas | 3.0 g | 1.05 |
| Deionized water | 74.4 g |  |

A solution of Aculyn® 44 was prepared by combining 3.0 g of the nonionic hydrophobically modified associative thickener with 74.4 g of deionized water and allowing it to hydrate by stirring at room temperature for 2 hours. The colored polymer solutions were then combined with the thickener solution by stirring at room temperature. The composition had a viscosity of 400 cP as measured with a Brookfield RVDV-III at 100 rpm. In the absence of Aculyn® 44, the viscosity of the composition described above was 3 cP when measured under the same conditions. The composition was applied to naturally blonde hair as described in Example 38. It produced a medium reddish brown shade. Other comments under Example 48 equally apply.

EXAMPLE 53

Comparative Example

|  | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 16) | 5.0 g | 1.5 |
| Blue Anthraquinone (30 WT % aqueous colored polymer solution). (Ex. 14) | 2.6 g | 0.78 |

-continued

Comparative Example

| | Weight of polymer solution and of other ingredients | % Weight of polymer in final composition |
|---|---|---|
| Aculyn ® 22 (30%, aqueous solution) Rohm and Haas | 1.66 g | 0.5 |
| Triton X-100 nonionic surfactant, Rohm and Haas | 0.1 g | |
| Triisopropanolamine | .55 g | |
| Deionized water | 75.73 g | |

A solution of Aculyn® 22 was prepared by combining 1.66 g of the ANIONIC hydrophobically modified associative thickener with 75.73 g of deionized water and adjusting the pH to 8.5 with triisopropanolamine in order to activate its rheological properties. The colored polymer solutions were then combined with the thickener solution and the Triton X-100 by stirring at room temperature. The composition had a viscosity of 400 cP as measured with a Brookfield RVDV-III at 100 rpm. In the absence of Aculyn® 22 and Triton X-100, the viscosity of the composition described above was 3 cP when measured under the same conditions. The composition was applied to naturally blonde hair as described in Example 38. It produced a medium reddish brown shade. Upon immersion in deionized water at room temperature, most of the color bled from the hair in about 2 minutes.

EXAMPLE 54

Comparative Example

| | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 16) | 5.0 g | 1.5 |
| Blue Anthraquinone (30 WT % aqueous colored polymer solution). (Ex. 14) | 2.6 g | 0.78 |
| Carbopol Ultrez-10, BF Goodrich | 0.3 g | |
| Triisopropanolamine | 0.7 g | |
| Deionized water | 76.4 g | |

A solution of Carbopol Ultrez-10 was prepared by combining 0.3 g of this cross linked polyacrylate (which is not a hydrophobically modified associative thickener) with 76.4 g of deionized water, allowing it to hydrate, and adjusting its pH to 6 with 0.7 g of triisopropanolamine in order to activate its rheological properties. The colored polymer solutions were then combined with the thickener solution by stirring at room temperature. The composition had a pH of 5.6 and a viscosity of 887 cP as measured with a Brookfield RVDV-III at 100 rpm. In the absence of this thickener, the viscosity of the composition described above was 3 cP when measured under the same conditions. The composition was applied to naturally blonde hair as described in Example 38. It produced a medium golden brown shade. It was observed that, while the hair showed a very small level of flaking when brushed and slight rub-off when rubbed against a white cloth, when the colored tresses were immersed in deionized water about 60% (measured spectrophotometrically) of the color deposited on the hair bled into the water in 10 minutes.

EXAMPLE 55

Comparative Example

| | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 16) | 5.0 g | 1.5 |
| Blue Anthraquinone (30 WT % aqueous colored polymer solution). (Ex. 14) | 2.6 g | 0.78 |
| Hydroxyethyl Cellulose (Cellosize QP-4400 Amerchol, Union Carbide) | 1.5 g | |
| Deionized water | 75.9 g | |

A solution of hydroxyethyl cellulose was prepared by combining 1.5 g of this thickener (which is not a hydrophobically modified associative thickener) with 75.9 g of deionized water and stirring at room temperature for 60 minutes. The colored polymer solutions were then combined with the thickener solution by stirring at room temperature. The composition had a viscosity of 1384 cP as measured with a Brookfield RVDV-III at 100 rpm. In the absence of this thickener, the viscosity of the composition described above is 3 cP when measured under the same conditions. The composition was applied to naturally blonde hair as described in Example 38. It produced a medium golden brown shade. It was observed that, while the hair showed a very small level of flaking when brushed and slight rub-off when rubbed against a white cloth, when the colored tresses were immersed in deionized water about 50% (measured spectrophotometrically) of the color deposited on the hair bled into the water in 10 minutes.

EXAMPLE 56

Comparative Example

| | Weight of polymer solution and of other ingredients | % Weight of polymer in final composition |
|---|---|---|
| Yellow Anthraquinone (30 WT % aqueous colored polymer solution). (Ex. 45) | 15.0 g | 4.5 |
| Red Anthraquinone (30 WT % aqueous colored polymer solution). (Ex. 16) | 5.0 g | 1.5 |
| Blue Anthraquinone (30 WT % aqueous colored polymer solution). (Ex. 14) | 2.6 g | 0.78 |
| Potassium Alginate Kelmar, Kelco | 1.5 g | |
| Deionized water | 75.9 g | |

A solution of potassium alginate was prepared by combining 1.5 g of this thickener (which is not a hydrophobically modified associative thickener) with 75.9 g of deionized water and stirring at 50° C. for 20 minutes. The colored polymer solutions were then combined with the thickener solution by stirring at room temperature. The composition had a viscosity of 452 cP as measured with a Brookfield RVDV-III at 100 rpm. In the absence of this thickener, the viscosity of the composition described above is 3 cP when measured under the same conditions. The composition was applied to naturally blonde hair as described in Example 38. It produced a medium golden brown shade. It was observed that, while the hair showed a very small level of flaking when brushed and slight rub-off when rubbed against a white cloth, when the colored tresses were immersed in deionized water about 75% (measured spectrophotometrically) of the color deposited on the hair bled into the water in 10 minutes.

While the invention has been described with particular reference to certain embodiments thereof, it will be understood that changes and modifications may be made which are within the skill of the art. The present invention is limited only by the claims that follow.

What we claim is:

1. A hair coloring composition comprising:
   (1) about 0.05 to about 40 weight % of at least one sulfo-containing, water-dispersible polymer having about 20 mole % to about 100 mole % carbonyloxy linking groups and 0% to about 80 mole % carbonylamide linking groups, and having a colorant reacted into or onto the backbone of the polymer;
   (2) about 0.05 to about 10 weight % of a nonionic, hydrophobically modified thickener; and
   (3) about 40 to about 99.90% of a vehicle consisting of water or water/alcohol with the provision that the alcohol is a $C_2$–$C_3$ alcohol and that the alcohol content does not exceed about 55% by weight of said hair coloring composition.

2. The composition of claim 1 wherein the colorant comprises one or more heat stable organic compounds having at least one condensable group, wherein the colorant is present in an amount from about 1 to about 40 mole %, based on the total of all reactant hydroxy, carboxy and amino equivalents and the condensable derivatives thereof.

3. The composition of claim 1 wherein the polymer, containing substantially equimolar proportions of acid equivalents to hydroxy and amino equivalents, comprises the reaction residues of the following reactants and their ester-forming or esteramide-forming derivatives:
   (a) at least one dicarboxylic acid;
   (b) from about 4 to about 25 mole %, based on a total of all acid, hydroxy and amino equivalents being equal to about 200 mole %, of at least one difunctional sulfomonomer containing at least one water solubilizing sulfonate group attached to an aromatic or cycloaliphatic nucleus wherein the functional groups are selected from the group consisting of hydroxy, carboxy and amino;
   (c) at least one difunctional reactant selected from a glycol or a mixture of a glycol and diamine having two —NHR groups, the glycol containing two —CH$_2$OH groups of which
      (1) at least about 10 mole %, based on the total mole percent of hydroxy or hydroxy and amine equivalents, is a poly(ethylene glycol) having the structural formula:

      H(OCH$_2$CH$_2$)$_n$OH n being an integer of from about 2 to about 20, or
      (2) from about 0.1 to about 15 mole %, based on the total mole percent of hydroxy or hydroxy and amine equivalents, is a poly(ethylene glycol) having the structural formula:

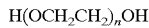
      H(OCH$_2$CH$_2$)$_n$OH n being an integer in the range from about 2 to about 500, and with the proviso that the mole percent of said poly(ethylene glycol) within said range is inversely proportional to the quantity of n within said range;
   (d) optionally, at least one difunctional reactant selected from a hydroxycarboxylic acid, an amino-carboxylic acid having one —NHR group or an amino-alcohol having one —C(R)$_2$OH group and one —NHR group; or mixtures of said difunctional reactants; wherein each R in the (c) or (d) reactants is a hydrogen atom or alkyl group of 1 to 4 carbon atoms; and
   (e) from about 5 to about 40 mole %, based on a total of all acid, hydroxy and amino equivalents being equal to about 200 mole %, of said colorant, wherein said colorant has at least one functional group selected from the group consisting of hydroxy, carboxy and amino equivalents, and the condensable derivatives thereof.

4. The composition of claim 3 wherein the carbonyloxy linking groups are polyesters and the carbonylamide linking groups are polyamides.

5. The composition of claim 1 wherein the nonionic thickener is selected from the group consisting of modified polycarbamyl polyglycol esters, modified hydroxyethyl cellulose and mixtures thereof.

6. The composition of claim 1 further comprising about 0.01 to about 10 weight % of one or more water-soluble nonionic or anionic surfactants.

7. A hair coloring composition comprising:
   (1) a tinctorially effective amount of one or more polymers comprising:
      (a) about 5 to about 100 weight %, based upon the total of component (1), of a colored, water-dispersible polymeric material having linking groups comprising about 20 mole % to about 100 mole % carbonyloxy and 0% to about 80 mole % carbonylamide, said polymeric material containing water-solubilizing sulfonate groups and having reacted into or onto the polymer backbone from about 1 to about 40 mole %, based on the total of all reactant hydroxy, carboxy and amino equivalents, and the condensable derivatives thereof, of colorant comprising one or more heat stable organic compounds initially having at least one condensable group; and
      (b) 0 to about 95 weight %, based upon the total of component (1), of an uncolored, water-dispersible polymeric material comprising:
         (i) about 50 to about 100 weight %, based upon the total of sub-component (b), of a water-dispersible polymeric material having linking groups comprising about 20 mole % to about 100 mole % carbonyloxy and 0% to about 80 mole % carbonylamide, said polymeric material containing water-solubilizing sulfonate groups; and
         (ii) 0 to about 50 weight %, based upon the total of sub-component (b), of a water-soluble vinyl polymer or copolymer which contains at least about 50 mole % of the residues of a vinyl lactam monomer having Formula I:

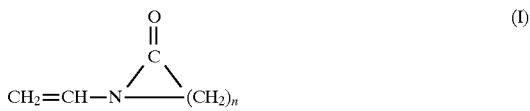

wherein n is 3 or 4;
   (2) about 0.05 to about 10 weight % of a nonionic hydrophobically modified thickener; and
   (3) about 40 to about 99.90 weight % of a vehicle consisting of water or water/alcohol with the provision that the alcohol is a $C_2$–$C_3$ alcohol and that the alcohol content does not exceed about 55% by weight of said hair coloring composition.

8. The composition of claim 7 wherein said colored, water-dispersible polymeric material comprises about 0.05 to about 40 weight % of said composition.

9. The composition of claim 8 comprising a copolymer of the vinyl lactam of Formula I and a vinyl monomer selected from the group consisting of $$CH_2=CH-OCR_3 \quad \overset{O}{\underset{\|}{}} \qquad (II)$$

$$CH_2=\underset{R_4}{\overset{|}{C}}-\overset{O}{\underset{\|}{C}}OR_5 \qquad (III)$$

and $$CH_2=\underset{}{\overset{R_4}{\underset{|}{C}}}-\!\!\!\!\bigcirc\!\!\!\!-R^6 \qquad (IV)$$

wherein $R_3$ is selected from $C_1$–$C_{10}$ alkyl groups; $R_4$ is hydrogen or methyl; $R_5$ is $C_1$–$C_{10}$ alkyl or $C_1$–$C_{10}$ alkylene-N($R_7$)$R_8$, wherein $R_7$ and $R_8$ are independently selected from the group consisting of hydrogen, $C_1$–$C_2$ alkyl and hydroxy $C_1$–$C_4$ alkyl; and $R_6$ is hydrogen or $C_1$–$C_6$ alkyl.

10. The composition of claim 9 wherein the carbonyloxy linking groups are polyesters and the carbonylamide linking groups are polyamides.

11. The composition of claim 7 wherein the nonionic thickener is selected from the group consisting of modified polycarbamyl polyglycol esters, modified hydroxyethyl cellulose and mixtures thereof.

12. The composition of claim 7 further comprising about 0.01 to about 10 weight % of one or more water-soluble nonionic or anionic surfactants.

13. A composition for coloring keratinous fibers comprising:
   (1) a tinctorially effective amount of a mixture of polymers comprising at least one polymer (a), at least one polymer (b)(i), and at least one polymer (b)(ii) as follows:
      (a) about 5 to 100 weight %, based upon the total of component (1), of a colored, water-dispersible polymeric material having linking groups comprising about 20 mole % to about 100 mole % carbonyloxy and 0% to about 80 mole % carbonylamide, said polymeric material containing water-solubilizing sulfonate groups and having reacted into or onto the polymer backbone from about 1 to about 40 mole %, based on the total of all reactant hydroxy, carboxy and amino equivalents, and the condensable derivatives thereof, of colorant comprising one or more heat stable organic compounds initially having at least one condensable group: and
      (b) a positive amount to about 95 weight %, based upon the total of component (1), of an uncolored, water-dispersible polymeric material comprising:
         (i) about 50 to 100 weight %, based upon the total of sub-component (b), of a water-dispersible polymeric material having linking groups comprising about 20 mole % to about 100 mole % carbonyloxy and 0% to about 80 mole % carbonylamide, said polymeric material containing water-solubilizing sulfonate groups; and
         (ii) a positive amount to about 50 weight %, based upon the total of sub-component (b), of a water-soluble vinyl copolymer of (x) at least about 50 mole % of the residues of a vinyl lactam monomer having Formula I:

$$CH_2=CH-N\overset{\overset{\displaystyle O}{\|}}{\underset{}{\overset{\displaystyle C}{\diagup\!\!\diagdown}}}(CH_2)_n \qquad (I)$$

wherein n is 3 or 4, and (y) a vinyl monomer selected from the group consisting of $$CH_2=CH-OCR_3 \quad \overset{O}{\underset{\|}{}} \qquad (II)$$

$$CH_2=\underset{R_4}{\overset{|}{C}}-\overset{O}{\underset{\|}{C}}OR_5 \qquad (III)$$

and $$CH_2=\underset{}{\overset{R_4}{\underset{|}{C}}}-\!\!\!\!\bigcirc\!\!\!\!-R^6 \qquad (IV)$$

wherein $R_3$ is selected from $C_1$–$C_{10}$ alkyl groups: $R_4$ is hydrogen or methyl; $R_5$ is $C_1$–$C_{10}$ alkyl or $C_1$–$C_{10}$ alkylene-N($R_7$)$R_8$, wherein $R_7$ and $R_8$ are independently selected from the group consisting of hydrogen, $C_1$–$C_2$ alkyl and hydroxy $C_1$–$C_4$ alkyl; and $R_6$ is hydrogen or $C_1$–$C_6$ alkyl; and
   (2) about 50 to about 99.95 weight % of a vehicle consisting of water or water/alcohol, with the provision that the alcohol is a $C_2$–$C_3$ alcohol and that the alcohol content does not exceed about 55% by weight of said composition.

14. The composition of claim 13 wherein the polymer, containing substantially equimolar proportions of acid equivalents to hydroxy and amino equivalents, comprises the reaction residues of the following reactants and their ester-forming or esteramide-forming derivatives:
   (a) at least one dicarboxylic acid;
   (b) from about 4 to about 25 mole %, based on a total of all acid, hydroxy and amino equivalents being equal to about 200 mole %, of at least one difunctional sulfomonomer containing at least one water solubilizing sulfonate group attached to an aromatic or cycloaliphatic nucleus wherein the functional groups are selected from the group consisting of hydroxy, carboxy and amino;
   (c) at least one difunctional reactant selected from a glycol or a mixture of a glycol and diamine having two —NHR groups, the glycol containing two —$CH_2$OH groups of which
      (1) at least about 10 mole %, based on the total mole percent of hydroxy or hydroxy and amine equivalents, is a poly(ethylene glycol) having the structural formula:

$$H(OCH_2CH_2)_nOH$$

n being an integer of from about 2 to about 20, or
      (2) from about 0.1 to about 15 mole %, based on the total mole percent of hydroxy or hydroxy and amine equivalents, is a poly(ethylene glycol) having the structural formula:

$H(OCH_2CH_2)_nOH$ n being an integer in the range from about 2 to about 500, and with the proviso that the mole percent of said poly(ethylene glycol) within said range is inversely proportional to the quantity of n within said range;

(d) optionally, at least one difunctional reactant selected from a hydroxycarboxylic acid, an amino-carboxylic acid having one —NHR group or an amino-alcohol having one —C(R)$_2$OH group and one —NHR group; or mixtures of said difunctional reactants; wherein each R in the (c) or (d) reactants is a hydrogen atom or alkyl group of 1 to 4 carbon atoms; and (e) from about 5 to about 40 mole %, based on a total of all acid, hydroxy and amino equivalents being equal to about 200 mole %, of said colorant, wherein said colorant has at least one functional group selected from the group consisting of hydroxy, carboxy and amino equivalents, and the condensable derivatives thereof.

15. The composition of claim 14 wherein said colored, water-dispersible polymeric material comprises about 0.05 to about 40 weight % of said composition.

16. The composition of claim 15 wherein the carbonyloxy linking groups are polyesters and the carbonylamide linking groups are polyamides.

17. The composition of claim 16 further comprising about 0.1 to about 10 weight % of an emulsifier.

18. The composition of claim 17 wherein the composition is a solution, lotion, mousse, spray, foam or gel.

* * * * *